United States Patent
Wu et al.

(10) Patent No.: US 10,307,144 B2
(45) Date of Patent: Jun. 4, 2019

(54) SUTURE DELIVERY DEVICE FOR SUTURING TISSUE

(71) Applicant: MEDEON BIODESIGN, INC., Taipei (TW)

(72) Inventors: I-Ching Wu, Los Altos, CA (US); Eric Y. Hu, Los Altos, CA (US); Po-Hua Lee, Los Altos, CA (US); Hsiao-Wei Tang, Taipei (TW); Shuling Cheng, Taipei (TW)

(73) Assignee: MEDEON BIODESIGN, INC., Taipei (TW)

( * ) Notice: Subject to any disclaimer, the term of this patent is extended or adjusted under 35 U.S.C. 154(b) by 373 days.

(21) Appl. No.: 14/615,786

(22) Filed: Feb. 6, 2015

(65) Prior Publication Data

US 2015/0223804 A1 Aug. 13, 2015

Related U.S. Application Data

(60) Provisional application No. 61/937,089, filed on Feb. 7, 2014.

(51) Int. Cl.
| | |
|---|---|
| *A61B 17/00* | (2006.01) |
| *A61B 17/04* | (2006.01) |
| *A61B 17/062* | (2006.01) |

(52) U.S. Cl.
CPC ...... *A61B 17/0057* (2013.01); *A61B 17/0482* (2013.01); *A61B 17/0625* (2013.01);
(Continued)

(58) Field of Classification Search
CPC ............ A61B 17/0057; A61B 17/0482; A61B 17/0625; A61B 2017/00637;
(Continued)

(56) References Cited

U.S. PATENT DOCUMENTS

| | | | |
|---|---|---|---|
| 5,830,232 A | 11/1998 | Hasson | |
| 5,984,948 A * | 11/1999 | Hasson | ............. A61B 17/0057 606/144 |

(Continued)

FOREIGN PATENT DOCUMENTS

| | | |
|---|---|---|
| EP | 2412317 A1 | 2/2012 |
| WO | 2010081106 A1 | 7/2010 |

OTHER PUBLICATIONS

International Searching Authority, Notification of Transmittal of the International Search Report and the Written Opinion of the International Search Authority, PCT/US2015/014797, dated May 7, 2015, pp. 1-9.

(Continued)

*Primary Examiner* — Martin T Ton
(74) *Attorney, Agent, or Firm* — Dergosits & Noah LLP; Todd A. Noah

(57) ABSTRACT

Systems are provided for delivering a suture to close a surgical opening. An elongated deployment member may have at its distal end a retracted counterforce member. The counterforce member may be inserted into the surgical opening and deployed to resist being withdrawn from the opening. A compression member may be slid down the elongated member to compress the tissue to be sutured against the counterforce member. Suture passers loaded with suture ends may be passed through needle tubes within the elongated member to emerge from the elongated member and pierce the tissue to be sutured, then deposit the suture ends with a suture catcher. The suture passers may be withdrawn, leaving the suture ends. The suture catcher may be retracted, retaining the suture ends and the device—elongated member, retracted suture catcher, and retained suture end—may be withdrawn from the surgical opening. The suture may then be completed.

20 Claims, 20 Drawing Sheets

(52) U.S. Cl.
CPC ............... *A61B 2017/00637* (2013.01); *A61B 2017/00663* (2013.01)

(58) Field of Classification Search
CPC ............ A61B 17/0469; A61B 17/0483; A61B 17/0493; A61B 2017/0472; A61B 2017/06042
USPC .................................................. 606/144, 148
See application file for complete search history.

(56) References Cited

U.S. PATENT DOCUMENTS

| | | | |
|---|---|---|---|
| 8,562,629 B2* | 10/2013 | Bain | A61B 17/0469 606/144 |
| 8,926,639 B2 | 1/2015 | Bagaoisan et al. | |
| 8,992,549 B2 | 3/2015 | Bennett, III | |
| 9,486,191 B2* | 11/2016 | Gianotti | A61B 17/0057 |
| 2004/0068273 A1 | 4/2004 | Fariss et al. | |
| 2006/0030868 A1 | 2/2006 | Bennett | |
| 2007/0203507 A1* | 8/2007 | McLaughlin | A61B 17/0057 606/144 |
| 2011/0082475 A1 | 4/2011 | Smith | |
| 2011/0270282 A1 | 11/2011 | Lemke | |
| 2012/0016385 A1 | 1/2012 | Keren et al. | |
| 2012/0035623 A1 | 2/2012 | Bagaoisan et al. | |
| 2012/0191109 A1 | 7/2012 | Rockrohr | |
| 2013/0035701 A1 | 2/2013 | Heneveld et al. | |
| 2013/0165956 A1* | 6/2013 | Sherts | A61B 17/0482 606/148 |
| 2013/0253543 A1 | 9/2013 | Heneveld | |
| 2013/0310856 A1 | 11/2013 | Sherts et al. | |
| 2015/0018850 A1 | 1/2015 | Bagaoisan et al. | |
| 2015/0157316 A1 | 6/2015 | Labarbera | |

OTHER PUBLICATIONS

Supplementary European Search Report and Written Opinion for European Application No. 15746966.9, dated Nov. 17, 2017.
International Search Report and Written Opinion for PCT Application No. PCT/US17/46347; dated Nov. 28, 2017.

* cited by examiner

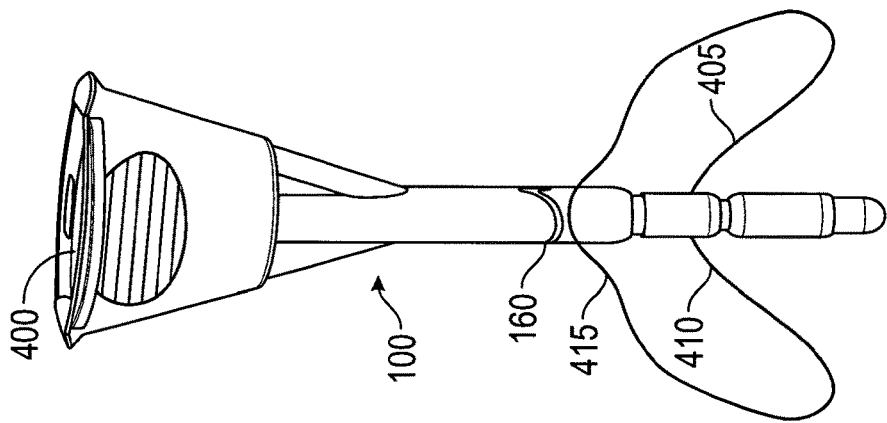
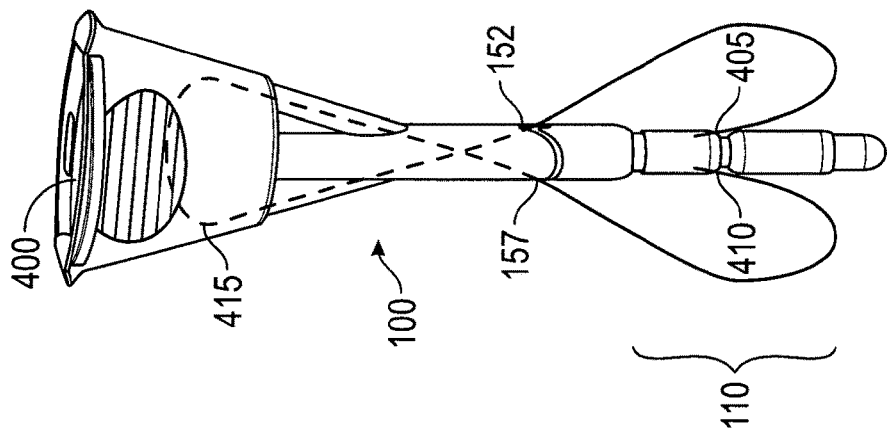
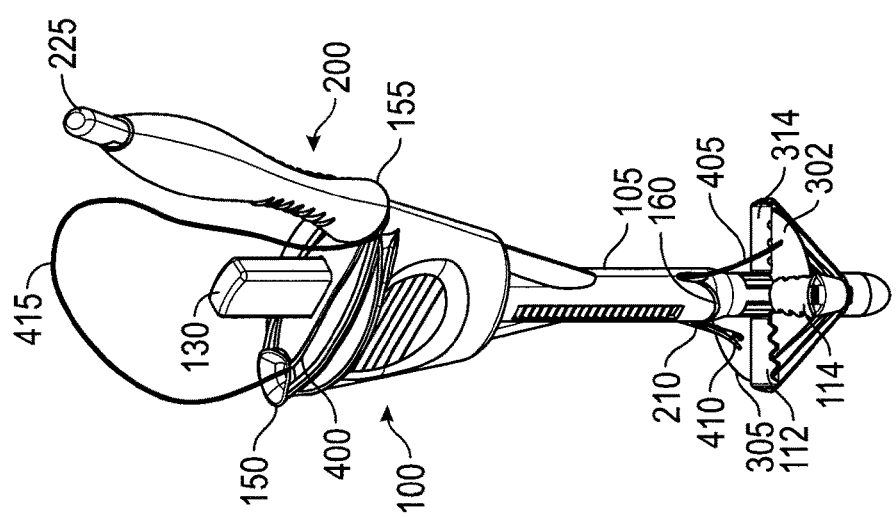

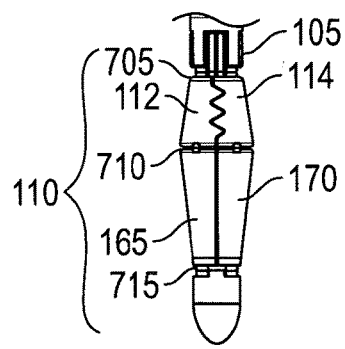
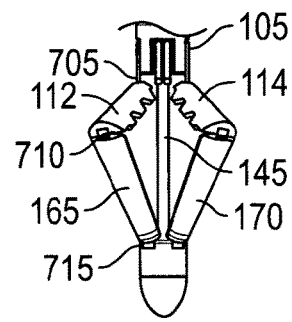
FIG. 6A    FIG. 6B
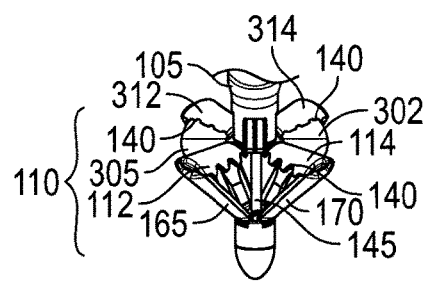
FIG. 6C
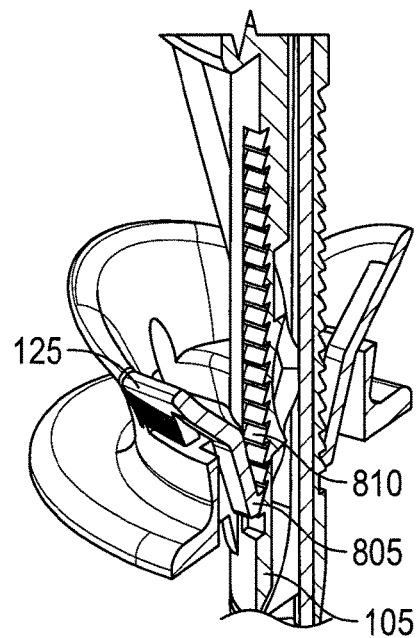
FIG. 7

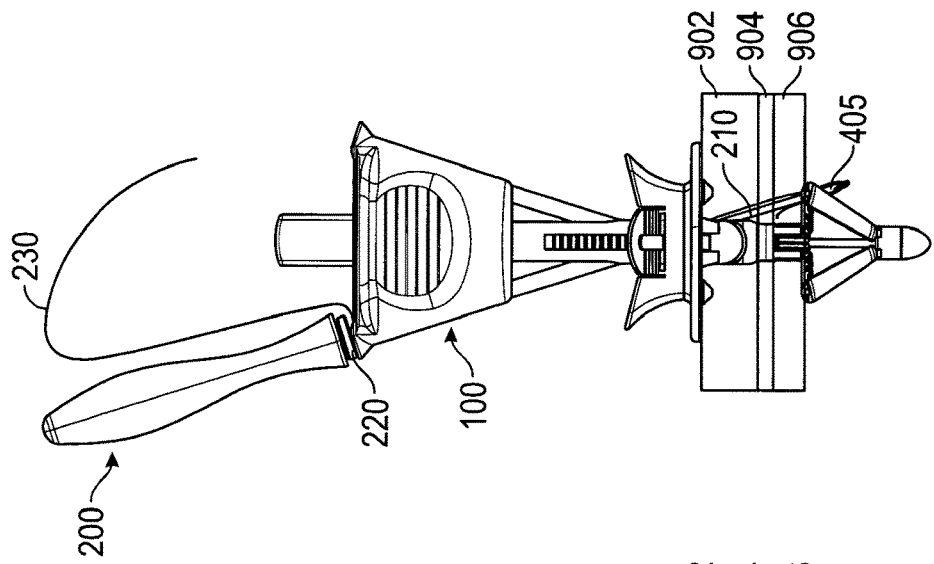
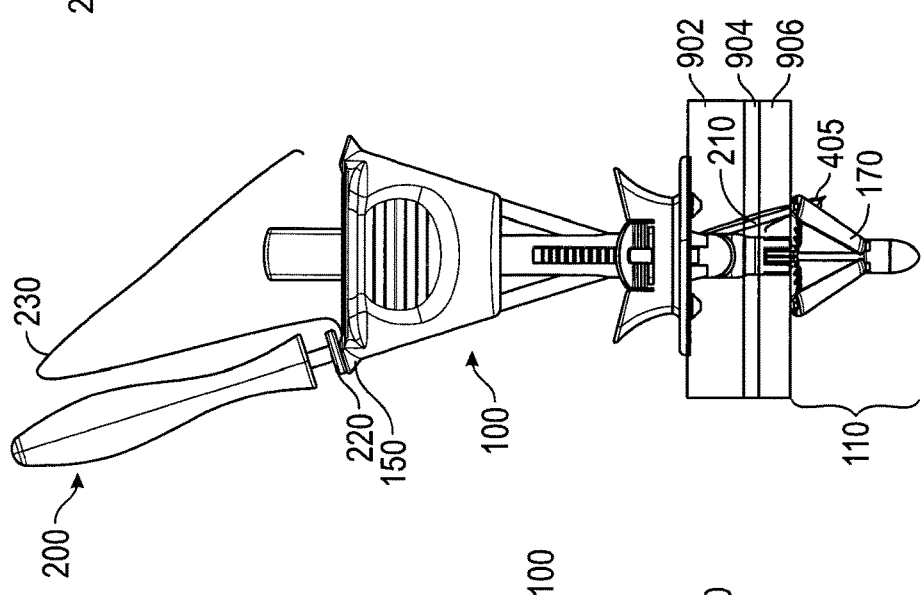
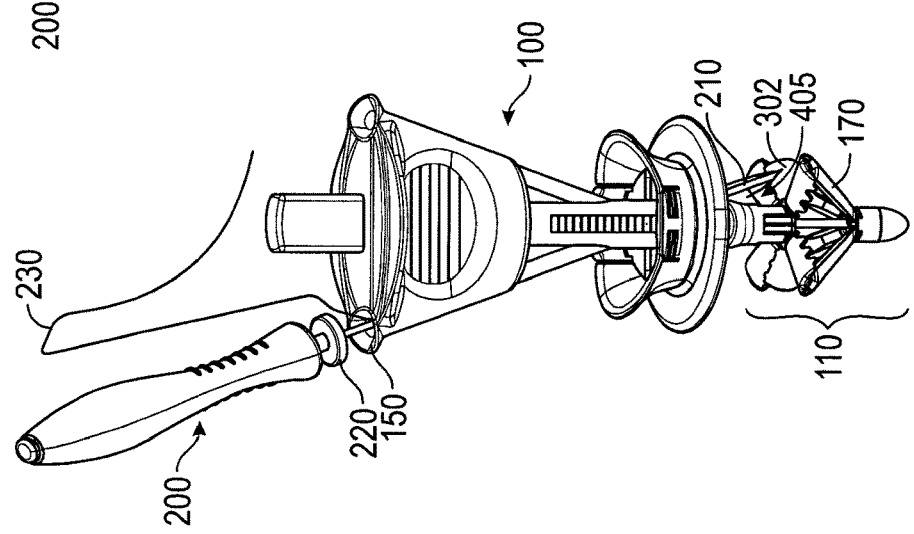

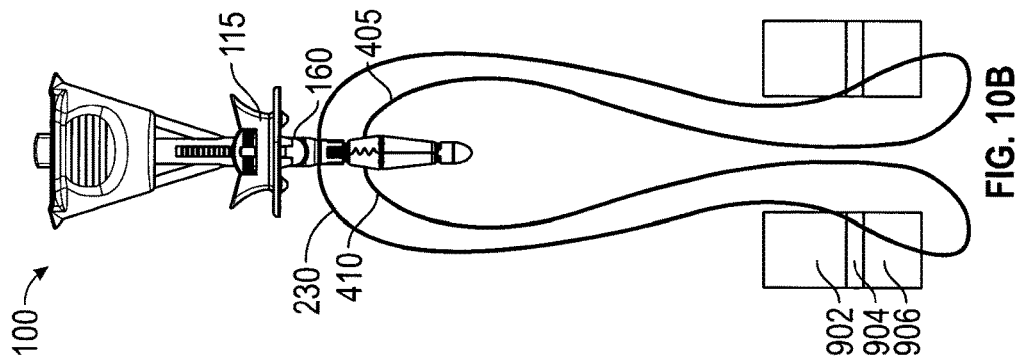
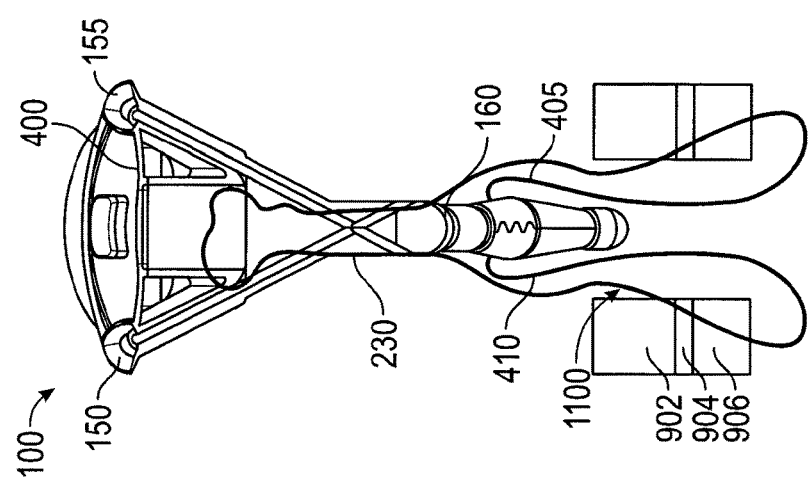
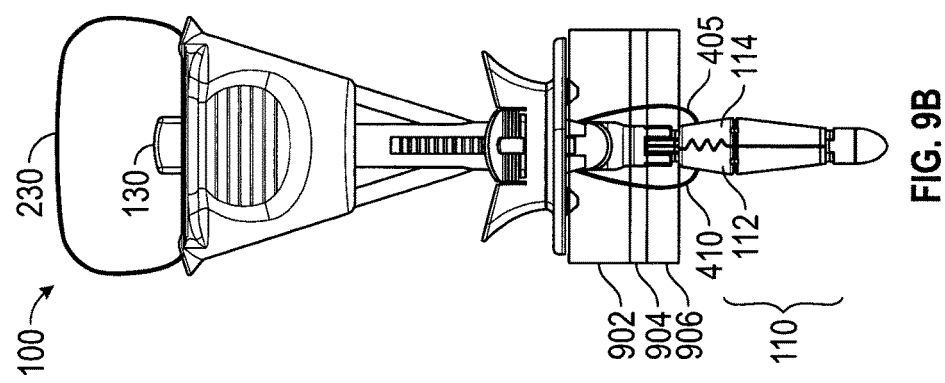

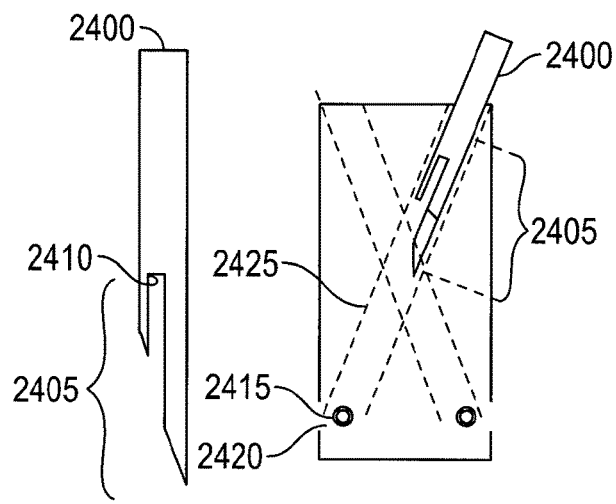
FIG. 22A
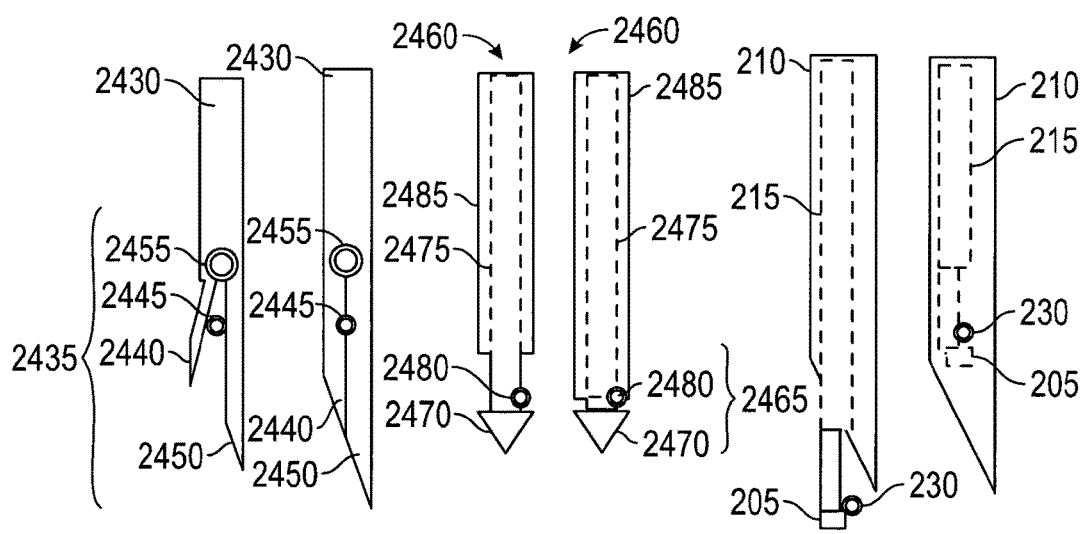
FIG. 22B  FIG. 22C  FIG. 22D

SUTURE DELIVERY DEVICE FOR SUTURING TISSUE

RELATED APPLICATIONS

This application claims priority to and benefit of U.S. Provisional Patent Application Ser. No. 61/937,089, filed Feb. 7, 2014, the contents of which are incorporated by reference in its entirety.

FIELD OF THE PRESENT DISCLOSURE

The present disclosure relates generally to techniques and devices for the closing of small incisions in a patient's body. For example, the present disclosure relates to systems, devices, and methods for the closure of laparoscopic port sites, which is needed following a variety of minimally invasive surgical procedures, e.g., a cholecystectomy, an appendectomy, or a bariatric surgery.

BACKGROUND

Laparoscopic surgery is a type of minimally invasive surgery. It is a substitute for traditional "open" surgeries and provides the benefits of minimizing post-operative pain, decreasing hospital stays and periods of disability, and reducing costs for both hospitals and patients.

Over 7.5 million laparoscopic surgeries are performed worldwide each year in the areas of, e.g., cholecystectomy, appendectomy, bariatric surgeries, gynecological surgeries, and urological surgeries. However, because of the incidence rate of port-site herniation for the laparoscopic surgeries, port-site closure is preferred for fascial incisions greater than or equal to 10 mm. Port-site closure can effectively reduce the rate of herniation, reducing the need for hernia repair surgery, which has estimated costs of between US$6,000-US$10,000 per procedure and three-week recovery times. Approximately 70% of the laparoscopic procedures performed have 10 mm or larger port-sites.

To ameliorate these problems, techniques for suturing the port site have been developed. Despite the benefits associated with the use of suture delivering devices, a number of challenges exist. Devices for port-site closure can rotate, tilt, and slide downward vertically in the wound track or incision during the insertion of a suture needle. If the device rotates, the suture will be deployed at less that the ideal 180 degree placement across the wound. If the device slides vertically during the insertion, the tissue bite of desired muscle/fascia layer is reduced for devices that use the peritoneum as a reference point for needle entry into the muscle/fascia layers. That is, if such a device is not engaged against the peritoneum due to downward sliding, the needle entry point into muscle/fascia layers will be lower than the intended position and reduce tissue bite. It is also desirable to provide a device configured to deploy the needles in a reproducible manner to minimize the amount of skill required from the operator. Accordingly, this disclosure is directed to systems and methods for wound closure that provide these and other desired characteristics.

SUMMARY

This disclosure includes a suture delivery device for suturing tissue. In an embodiment, the delivery device includes an elongated deployment member. Towards the distal end of the elongated deployment member, a counterforce member is configured to transition between a retracted configuration that facilitates the counterforce member entering an incision and a deployed configuration that resists extracting the counterforce member from an incision. Towards the proximal end of the elongated deployment member, a compression member is configured to resist entering an incision. The compression member and the counterforce member transition between a compressed configuration and an uncompressed configuration. In the compressed configuration, tissue may be sandwiched between the compression member and the counterforce member to stabilize the device. A suture catcher disposed towards the distal end of the elongated deployment member is configured to transition between a retracted configuration that facilitates the suture catcher entering an incision and a deployed configuration that facilitates catching a suture. A first needle track is associated with the elongated deployment member and is oriented towards a first area of the suture catcher when in the deployed configuration. A second needle track is also associated with the elongated deployment member and is oriented towards a second area of the suture catcher when in the deployed configuration. The first area of the suture catcher when in the deployed configuration and the second area of the suture catcher when in the deployed configuration are situated on the suture catcher to allow their placement on opposite sides of an incision. The first and second needle tracks may pass through the elongated deployment member.

In an embodiment, the compression member is configured to resist entering an incision, and is position-able along the elongated deployment member to transition between a compressed configuration and an uncompressed configuration.

In an embodiment, the compression member is configured to resist entering an incision, and is position-able along the elongated deployment member to transition between a compressed configuration and an uncompressed configuration. This embodiment also includes a counterforce member that is configured to transition between a retracted configuration that facilitates the counterforce member entering an incision and a deployed configuration that resists extracting the counterforce member from an incision. In this embodiment, the counterforce member also includes a suture catcher.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which:

FIGS. 4A-4C depict an embodiment of a suture delivery device with a suture escape slot;

FIGS. 6A-6C depict an embodiment of a suture catcher;

FIG. 7 depicts a cross-sectional perspective view of a section of an embodiment of a suture delivery device;

FIGS. 8A-8G depict stages in the use of an embodiment of a suture delivery device handle and suture passer;

FIGS. 9A and 9B depict a side view of stages of retracting an embodiment of a suture catcher;

FIGS. 10A and 10B depict an embodiment for automatically releasing a suture;

FIGS. 22A-22D depict embodiments of a suture passer tip;

DETAILED DESCRIPTION

Figure 1A:
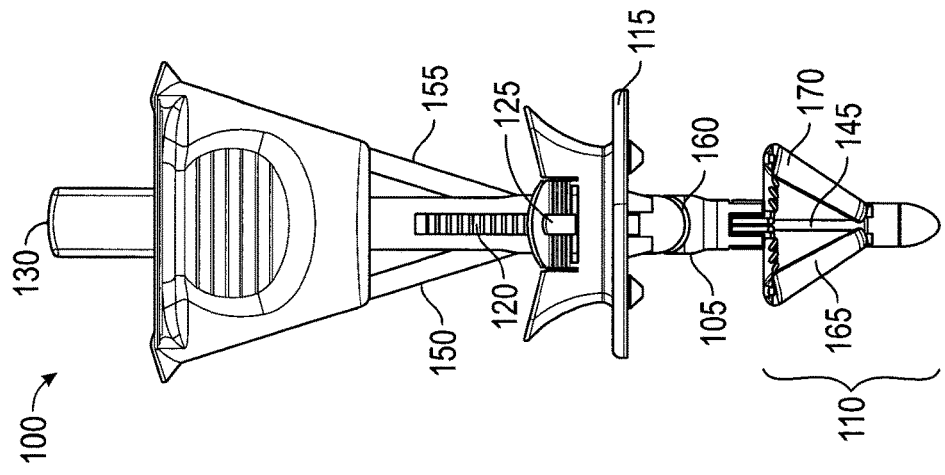
FIGS. 1A and 1B depict a side view of an embodiment of a suture delivery device handle.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains. For example, the term "suturing" includes drawing two surfaces or edges together with a flexible material to close a puncture, opening, or other wound, wherein the suture is a material that may be synthetic or natural, such as a polymer, gut, metallic wire or other suitable equivalents.

As used in this specification and the appended claims, the singular forms "a, "an," and "the" include plural referents unless the content clearly dictates otherwise.

Embodiments within describe a suture delivery device that may be inserted into the same opening used to perform a surgical procedure, such as laparoscopic surgery. The suture delivery device decreases the potential for tilting, rotating, or sliding relative to the opening by compressing the surrounding tissue, thereby stabilizing the device within the opening. Thus stabilized, the suture delivery device is able to improve tissue bite by reliably directing a suture to a pre-determined tissue area or layer. The suture delivery device may be used to orient one or more suture passers, which pass through the body of the delivery device to pierce through the port-site tissue and release the suture after the piercing. The suture delivery device captures the sutures and, upon withdrawing the delivery device, the suture ends are drawn back through the opening so that the suture may be secured and the opening closed. Embodiments are easy to use, which is important for a tissue closure device, which may be a last step in long, tiring surgical procedure.

Figure 1B:
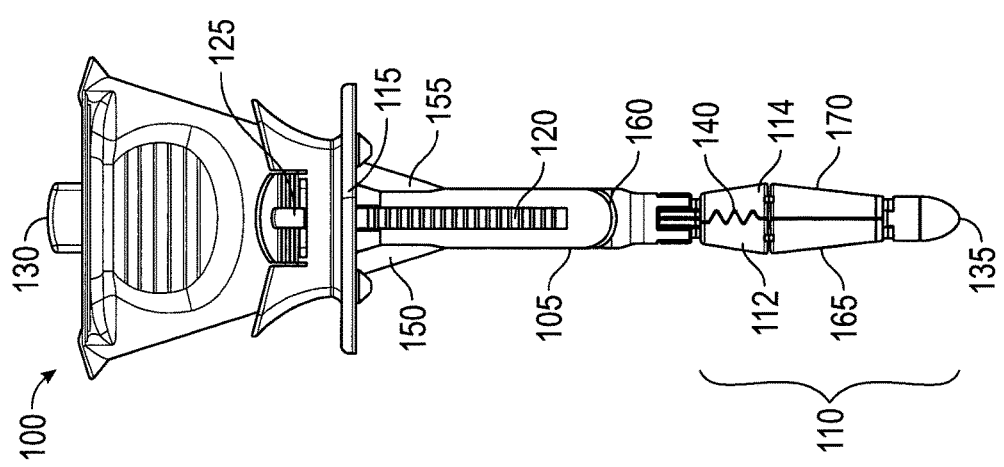
Figure 2B:
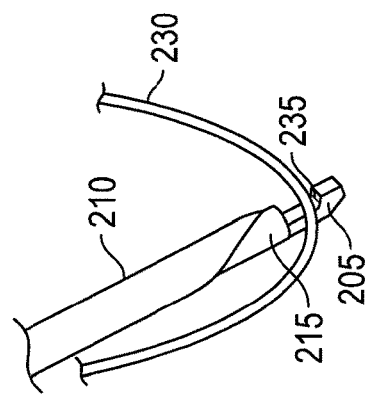
FIGS. 2A-2C depict perspective views of an embodiment of a suture passer.
Figure 2C:
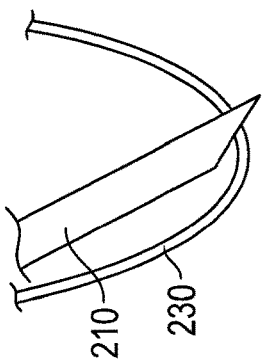
Figure 2A:
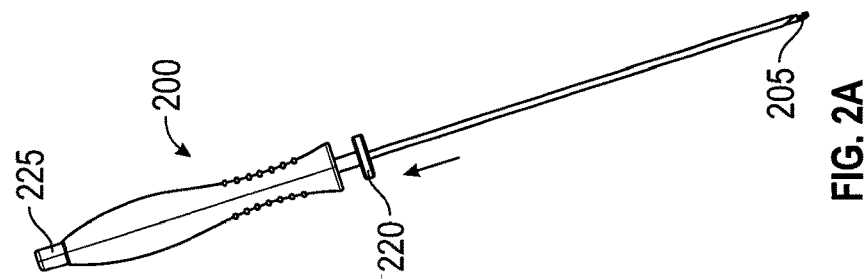

A suture delivery device (or "wound closure device," or "trocar wound closure device" (TWC)) generally has two parts: a handle 100 (FIGS. 1A, 1B) and a suture passer (FIGS. 2A-2C). FIGS. 1A and 1B depict two configurations of an embodiment of a suture delivery device handle 100. The configuration in FIG. 1A is used when the device is inserted into an opening. In FIG. 1A, handle 100 is in an uncompressed configuration. FIG. 1A depicts handle 100 with a shaft 105, a catcher 110 (including catcher elements 112, 114), a slider 115, needle tracks 150, 155, and a suture exit slit 160. Shaft 105 is an elongated deployment member equipped with a ridged track 120. Slider 115 is a compression member that may be moved along shaft 105 toward a distal end 135 and fixed in position by engaging track 120. Anti-rotation bumps, not shown, along with track 120 prevent slider 115 from rotating relative to needle tracks 150, 155 (FIG. 1B). Slider button 125 may be used to engage or disengage track 120. Catcher 110, shown closed, is a counterforce member when deployed and may include teeth 140, which may close about and grasp a suture. Control button 130, shown depressed, moves a control rod 145 (FIG. 1B), which opens (or deploys) or closes catcher 110 by moving struts 165, 170. With catcher 110 closed, distal end 135, catcher 110, and shaft 105 may be inserted into a surgical opening until catcher 110 is through the opening, at which point catcher 110 may be deployed as shown in FIG. 1B.

In FIG. 1B, handle 100 is in a compressed configuration, with control button 130 shown released, control rod 145 visible, catcher 110 deployed, and slider 115 moved distally. To deploy catcher 110, control button 130 is released, to move control rod 145 proximally (i.e., toward control button 130, or "up" in this view), causing struts 165, 170 to deploy catcher 110. To move slider 115 either proximally or distally, slider button 125 is used to disengage slider 115 from track 120 and then slider 115 may then be moved. Optionally, slider 115 may ratchet distally along shaft 105, with slider button 125 used to disengage slider 115 from track 120 and move slider 115 proximally (see FIG. 7).

The configuration in FIG. 1B may compress tissue between slider 115 and catcher 110. For example, the fascia, muscle and peritoneum layer of an abdominal wall may be compressed between slider 115 and catcher 110, with the peritoneum nearest to catcher 110. As shown deployed, catcher 110 would resist being pulled through the opening in the abdominal wall. Thus, in this embodiment, catcher 110 is a counterforce member. In other embodiments, a counterforce may be applied by elements that lack suture catching capabilities. Similarly, in other embodiments, suture-catching capability may be supplied by elements that lack counterforce capability.

In this configuration, with tissue compressed between slider 115 and catcher 110, handle 100 is stabilized relative to the compressed tissue, reducing the potential for rotation, sliding, or tilting. Furthermore, with handle 100 stabilized, needle tracks 150, 155 are also stabilized relative to the surrounding tissue, which is the tissue to be sutured. This provides for the optimal placement of sutures and for deploying sutures in a reproducible manner, both of which work to ensure proper tissue bite and minimize the amount of skill required from an operator.

FIGS. 2A-2C depict an embodiment of a suture passer 200. Suture passer 200 is used to grasp a suture end and pass the suture through a needle track, e.g., needle track 150, to position the suture so it may be caught by catcher 110. Suture passer 200 includes a hook 205 at a distal end, a needle tube 210, a shaft 215, a trigger 220, and a needle button 225. Hook 205 is at the distal end of shaft 215. Needle tube 210 has a point at the distal end and may move relative to shaft 215 to cover or uncover hook 205. Hook 205 is configured to accept a suture 230 (see FIG. 2B) and, when covered by needle tube 210, retain the suture (see FIG. 2C). Hook 205 may have a blunt tip—a point not being necessary while loading the suture. Hook 205 may also have a ramp 235 that allows a suture to slide off when hook 205 is uncovered. In FIG. 2A, needle button 225 is shown extended (not pressed) and hook 205 is shown uncovered. Needle button 225, when pressed, may extend needle tube 210 over hook 205 to retain a suture. Trigger 220, when pressed, may result in needle tube uncovering hook 205 to release a suture. Needle tube 210, shaft 215, hook 205, and trigger 220 are configured to fit within needle tracks 150, 155 and to deliver and release a suture in a desired location relative to a deployed catcher 110.

FIGS. 2B and 2C generally depict the loading of suture passer 200. Suture passer 200 has two states that are controlled by needle button 225 and trigger 220. In the initial "off" state shaft 215 and hook 205 protrude from the needle tube 210. Hook 205 is used to receive the suture in this configuration. That is, suture 230 may be positioned to be grabbed by hook 205. To transition to an "on" state, a user presses needle button 225, which causes needle tube 210 to extend to cover suture 230 and hook 205. Thus, shaft 215, hook 205, and needle tube 210 cooperate to retain or grasp suture 230. To return to the "off" state, trigger 220 may be activated by pressing it in the proximal direction. Pressing trigger 220 may thereby release suture 230.

Figure 3:
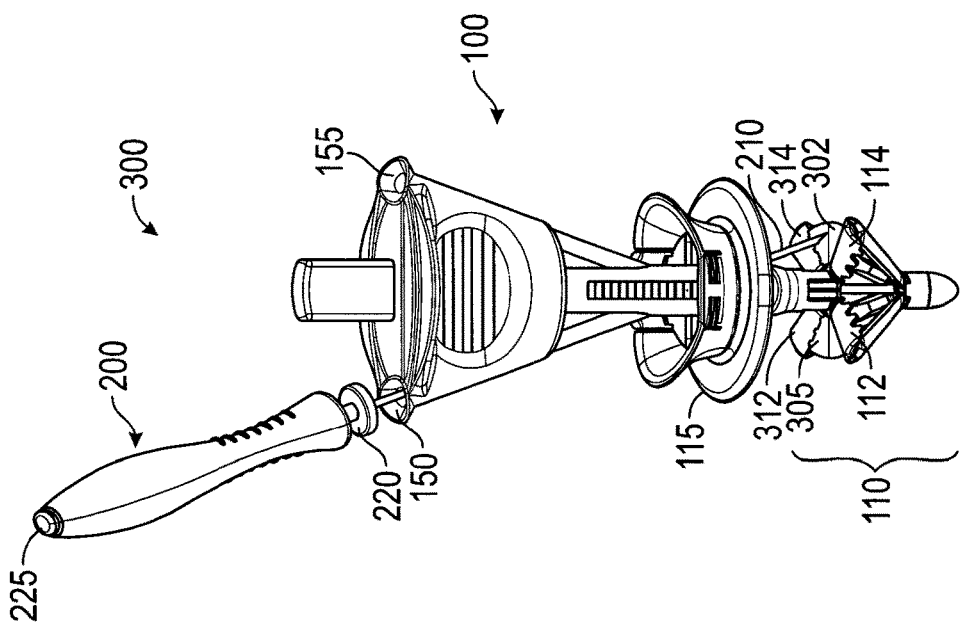
FIG. 3 depicts a perspective view of an embodiment of a suture delivery device handle with suture passer inserted.

FIG. 3 depicts a suture delivery device 300. In FIG. 3 suture passer 200 inserted into needle track 150 of handle 100. Handle 100 is in a compressed configuration with catcher 100 deployed and slider 115 moved distally. Needle button 225 is shown depressed, with needle tube 210 covering hook 205 (not shown). The distal tip of needle tube 210 is near a membrane 302. Membrane 302 extends between catcher elements 114 and 314. Membrane 305 extends between catcher elements 112 and 312.

As shown in FIG. 3, needle track 150 has oriented suture passer 200 to point to an area between catcher elements 114 and 314 of deployed catcher 110. In this embodiment, catcher 110 has been provisioned with membrane 302 in that area. Membrane 302 is added to improve the ability of catcher 110 to catch a suture. If suture passer 200 is inserted further into needle track 150 the sharp point of needle tube 210 would pierce membrane 302, carrying a suture (not shown) with it. Further insertion would cause trigger 220 to touch the opening of needle track 150. Still further insertion would cause trigger 220 to actuate and cause needle tube 210 to retract, exposing hook 205 and releasing the suture (not shown). At that point, suture passer 200 could be withdrawn from needle track 150. Withdrawing suture passer 200 from the needle track would also withdraw it from membrane 302. But the suture, having been released from hook 205, would be retained within membrane 302. Then, if catcher 110 is then retracted, membrane 302 is also retracted, bringing the suture with it to be grasped by catcher elements 114, 314. This is described further with respect to FIGS. 9A and 9B.

FIGS. 4A-4C depict an embodiment of a handle 100 providing automatic suture release. When two ends of a single suture are delivered into a surgical opening and retained at the distal end of the suture deliver device, the portion of the suture near the proximal end forms a loop. The loop could become entangled with the device during device retrieval. Existing closure devices allow for the operator to manually disengage the suture from the device. The embodiment of FIGS. 4A-4C uses an internal suture escape slot 400 that facilitates the automatic release of suture 415. Suture escape slot 400 connects needle tracks 150, 155 throughout their length, providing a slot for a suture 415 to pass through handle 100 and out suture exit slot 160. In FIG. 4A, suture passer 200 is inserted in needle track 155 and extends from shaft 105 exposing needle tube 210. Needle tube 210 is shown after piercing membrane 305. A suture tip 410 of suture 415 is shown also passing through membrane 305, having been carried through by the tip of suture passer 200. Control button 130 is shown extended. Thus, needle tube 210 is not covering hook 205 and suture end 410 is released from suture passer 200 (though the needle tip is obscured in FIG. 4A by membrane 305). Needle track 150 shows suture 415 after suture end 405 has been passed through membrane 302, released, and suture passer 200 withdrawn. As shown in FIG. 4A, both suture ends 405, 410 are retained by membranes 302, 305. From suture end 405, suture 415 passes through and out of needle track 150, loops over handle 100, and, accompanied by suture passer 200, enters needle track 155. In FIGS. 4A-4C, slider 115 is not shown to more clearly explain the internal suture escape path.

In FIG. 4B, suture passer 200 has been withdrawn from needle track 155 and catcher 110 has been retracted, grasping suture ends 405, 410. Handle 100 may be withdrawn from a surgical opening in this configuration, pulling suture ends 405, and 410 with it. Suture 415 makes a loop between a needle track exit 152 and catcher 110. Suture 415 also makes a loop between a needle track exit 157 and catcher 110. These loops represent portions of suture 415 that have passed through the tissue to be sutured. Thus, when handle 100 is removed from the surgical opening, pulling suture ends 410, 415 with it, the sections of suture 415 looped through the tissue will pull the remainder of suture 415 down through suture escape slot 400 (as shown, dotted). In 4C, suture 415 has passed completely through suture escape slot 400 and out suture exit slot 160.

Thus, with reference to FIGS. 1-4, embodiments of handle 100 of suture delivery device 300 may include needle track elements, e.g., needle tracks 150, 155, and a suture retention element, e.g., catcher 110. The needle track elements may extend from the proximal end towards distal end of handle 100 and may include an auto suture release mechanism, e.g., suture escape slot 400. The suture retention element may be disposed at or near the distal end of handle 100. The suture delivery device may also have a compressive element, e.g., slider 115.

The needle track elements may provide defined trajectories for needles (e.g., suture passer 200) inserted through the handle (e.g., handle 100), beginning near the proximal end and exiting near the distal end. For example, with the handle inserted into a surgical opening, a needle may enter the proximal end of a needle track element (e.g., needle track 150) above the skin, travel through the needle track in the device, and exit at the distal end to penetrate through tissues layers (such as fascia, muscle, and peritoneum) at defined position and angle relative to the handle. The needle trajectory may be completely enclosed by the handle between entry and exit. The needle track element may be coupled with an auto suture release mechanism (described with reference to FIGS. 4A-4C) whereby the suture loop (or main section of the suture, excluding the suture ends) is not retained at the device's distal end and may slide out, without user intervention, from the needle track as the handle is withdrawn from the surgical opening.

The suture retention element (e.g., catcher 110) may comprise a frame (e.g., catcher elements 112, 114, 312, 314) and suture capture surface(s) (e.g., membranes 302, 305) or a frame only. The suture retention element may be provided with features to improve its grip on the suture (e.g., teeth 140). The suture retention element frame may have multiple struts and may have various geometries (e.g., flat, lantern, molly, umbrella, etc.). The suture retention element frame may define a target area and may provide a counterforce to the compressive force of the compressive element, sandwiching the tissue in between. This counterforce may be against, for example, the peritoneum. The suture retention element may also provide support to an optional suture capture surface during needle insertion. The suture retention element may be inserted through the tissue opening in a low profile or retracted state and deployed to its expanded state after passing through tissue layers to the intended position, which may be, for example, inside the peritoneal cavity. The suture capture surface may be coupled to the struts of the frame, and may be in a folded configuration during device insertion as well as during device withdrawal.

A needle (e.g., suture passer 200) carrying a suture may be introduced into a needle track element (e.g., needle track 150), guided to penetrate through tissue layers (e.g., past the peritoneum), and inserted into the catcher (e.g., positioned between catcher elements 112, 312, or inserted into membrane 305). The design of the distal tip of the needle may allow the suture to be disengaged from the needle (e.g., hook 205 may have a ramp 235 that allows suture 230 to slide off, rather than a true "hook"). In some embodiments, the needle may be triggered to release the suture from its tip when the needle is inserted to an intended position.

In embodiments, the needle tip design (e.g., ramp 235) may allow the suture to disengage from the needle. In embodiments with a capture surface (e.g., membranes 302, 305), the surface itself may have a property or a design that enhances the capture and retention of suture by the surface, which assists disengaging the suture from the needle.

The device may be withdrawn from the surgical opening (e.g., a trocar wound) while retaining the captured suture ends at the distal end of device (e.g., in the catcher).

In an embodiment, the membrane is essentially enclosed by the catcher frame during the insertion and withdrawal of the catcher through tissue layers. In embodiments, the suture ends may be captured in the membrane as well as held between struts of the closed catcher frame. In an embodiment in which the suture retention element includes a frame, the suture ends may be retained by mechanical clamping between struts of the closed frame during device retrieval.

The suture delivery device may also have a compressive element, e.g., slider 115, that is movable along the device shaft to adapt for varying anatomy. The compressive element may be placed in a position that sandwiches tissue against a counterforce member (e.g., catcher 110). For example, the tissue may be the layers of the abdominal wall, the counterforce member may be positioned in the abdominal cavity against the peritoneum, and the compressive element may be against the surface of the skin. The compressive element thereby stabilizes the tissue while adapting to varying anatomy. In some embodiments, the compressive element may be linked to a counterforce member deployment mechanism so that movement of the compressive element causes the counterforce member to deploy and retract.

Figure 5A:
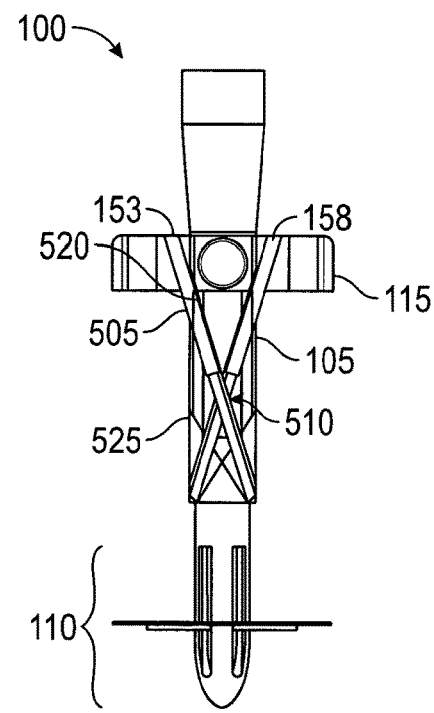
FIGS. 5A and 5B depict cross-sections of an embodiment of a suture delivery device with telescoping needle tracks.
Figure 5B:
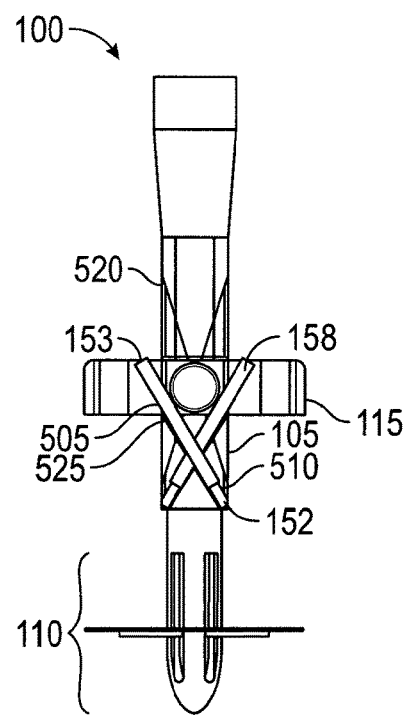

FIGS. 5A and 5B show cross-sections of an embodiment of handle 100 with telescoping needle tracks 153, 158. In FIG. 5A, handle 100 is in an uncompressed configuration with slider 115 extended proximally, away from catcher 110. For simplicity, and because telescoping needle tracks 153, 158 are similar, only telescoping needle track 153 will be described. Telescoping needle track 153 includes a pair of tubes 505, 510 configured to telescope, tube 510 within tube 505. In an embodiment (not shown), tube 505 moves within tube 510, so that a suture passer would avoid hitting the end of tube 510 when inserted. In FIGS. 5A and 5B, tube 505 is anchored at the non-telescoping end to slider 115. Tube 510 is anchored at the non-telescoping end to shaft 105. The anchor attachments allow angular motion between the tube and anchor point. In FIG. 5B, handle 100 is in a compressed configuration with slider 115 moved distally, toward catcher 110. With that motion, telescoping needle tracks 153, 158 have shortened in length and changed the angle at which they exit handle 100. Still, telescoping needle tracks 153, 158 are oriented to direct a suture passer towards catcher 110. In the movement of slider 115 from the uncompressed to compressed configuration, telescoping needle track 153 has swept out a volume within shaft 105 bounded by an upper limit 520, a lower limit 525, and needle track exit 152. In this embodiment, handle 100, shaft 105, and slider 115 are configured to permit this motion of telescoping needle tracks 153, 158.

In a method of using an embodiment, handle 100 is initially in the uncompressed and retracted configuration. In a first step, handle 100 is inserted into the trocar wound. In a next step, control button 130 is pressed to open the catcher 110. In a next step, handle 100 is pulled up against the tissue until the catcher 110 is in contact with the peritoneum. In a next step, slider 115 is pushed down to sandwich the abdomen wall against the catcher 110. The handle is then stabilized within the tissue to be sutured. In a next step, one end of suture 230 is loaded onto hook 205 and needle button 225 is pressed. In a next step, suture passer 200 is inserted into a needle track and trigger 220 is activated, releasing suture 230. In a next step, suture passer 200 is withdrawn from handle 100. In a next step, a second end of suture 230 (or the end of a different suture) is loaded onto hook 205 and the previous two suture-passing steps repeated in a different needle track. Handle 100 may now be withdrawn, taking with it the suture ends according to the following steps. In a next step, control button 130 is pressed to capture the suture ends with catcher 110 (the suture ends may also have been retained by optional membranes 302, 305). In a next step, handle 100 is withdrawn from the surgical opening, bringing with it the suture ends. The suture ends are then removed from handle 100 and knotted.

FIGS. 6A-6C depict an embodiment of a suture catcher 110 in retracted, partially deployed, and fully deployed configurations, respectively. In FIG. 6A, suture catcher 110 has hinge joints 705, 710, 715, struts 165, 170 and catcher elements 112, 114. Joints 705, 710, 715 may be a mechanical, or a living hinge, or a combination. In FIG. 6B, catcher 110 has been expanded to a partially deployed status by using control rod 145 to urge struts 165, 170 against catcher elements 112, 114. Catcher elements 312, 314 have been similarly deployed. In FIG. 6C, catcher 110 has been fully deployed using control rod 145. FIG. 6C also shows optional membranes 302, 305 attached to catcher elements 112, 114. Control button 130 (FIGS. 1 and 3) may be connected to control rod 145 and used to activate control rod 145.

FIG. 7 depicts in cross-section a section of an embodiment of handle 100. In the embodiment of FIG. 7, slider 115 may move easily toward the distal direction, but not toward the proximal direction, using a ratchet 805 and rack 810. Thus, slider 115 may easily move toward a compressed configuration, but not an uncompressed configuration. In the embodiment, pushing slider button 125 releases ratchet 805, allowing slider 115 to move proximally. Rack 810 may include a lower limit (not shown) that prevents the slider from moving too far in the compressive direction. In an embodiment, a friction pad (not shown) is used between slider 115 and shaft 105. The shape of the friction pad is designed to modulate pushing friction in two directions.

Figures 8D, 8E:
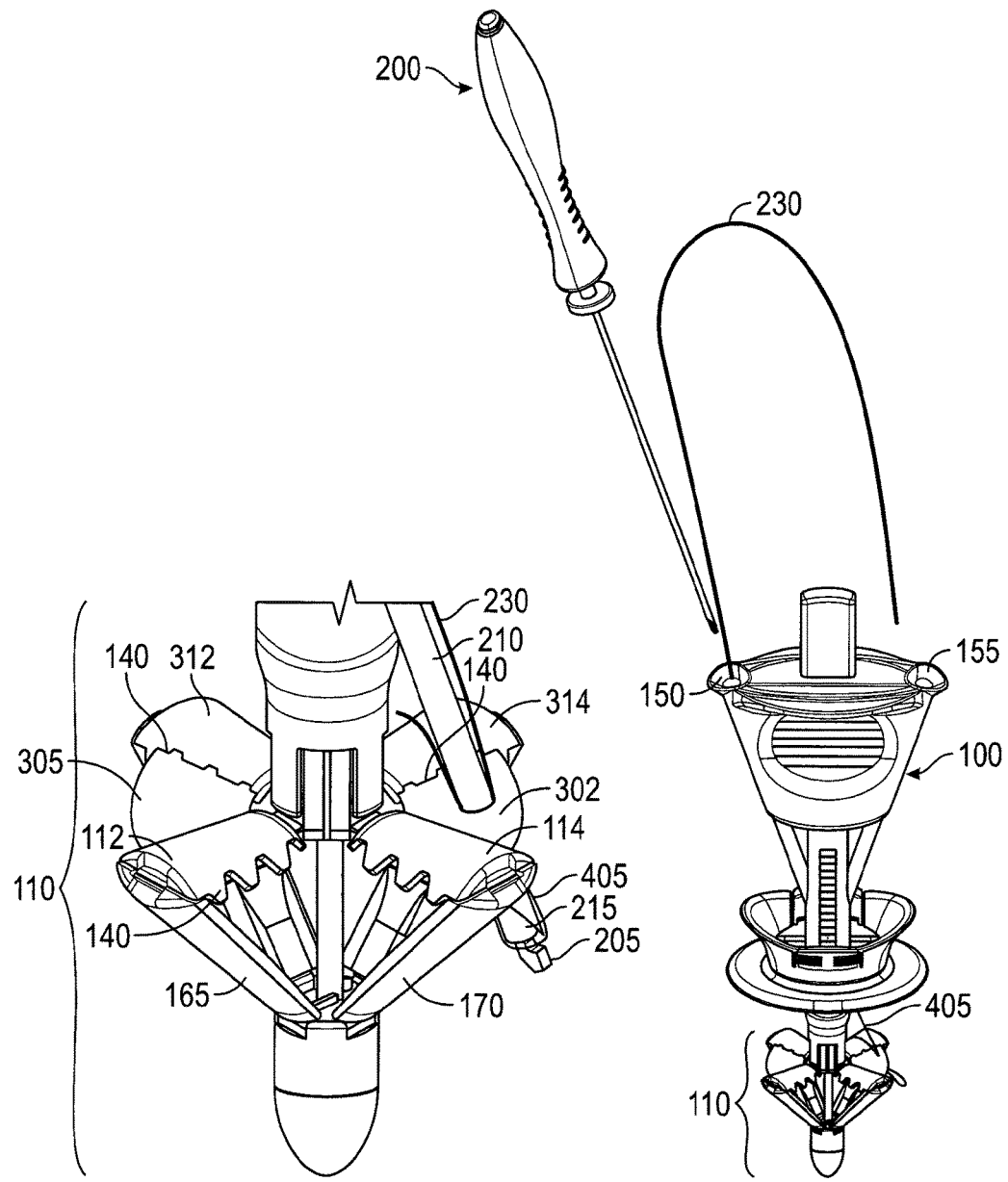
Figure 8G:
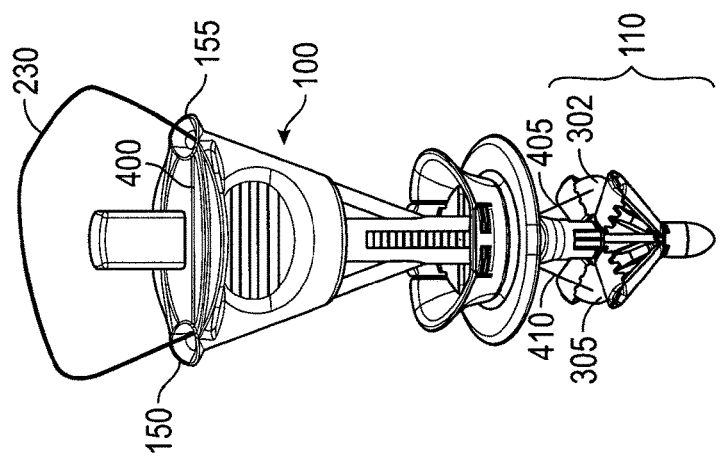
Figure 8F:
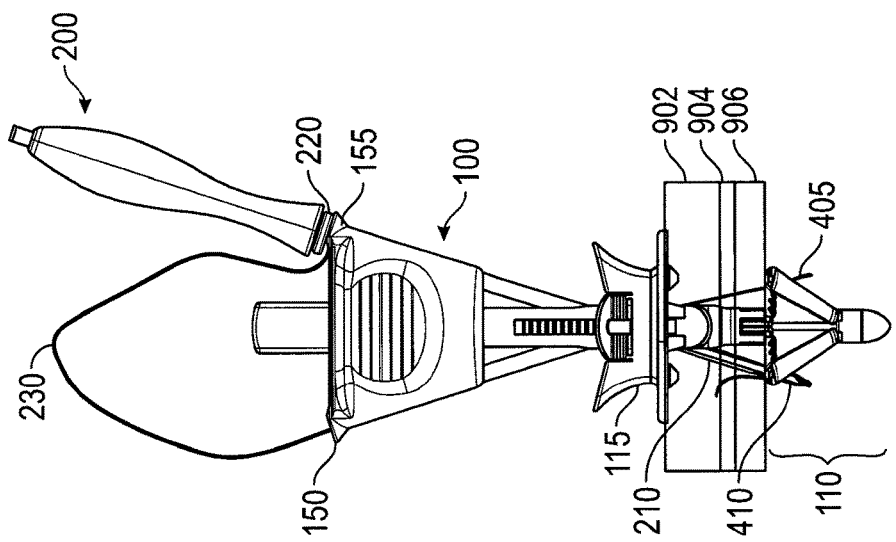

FIGS. 8A-8G depict an embodiment in the various stages of deploying a suture. FIG. 8A is a perspective view of a loaded suture passer 200 inserted into needle track 150. In FIG. 8A, catcher 110 is in the deployed configuration. Needle tube 210, grasping suture end 405, has exited needle track 150, but has not yet penetrated membrane 302. In FIG. 8B, suture passer 200 has been further inserted into needle track 150 so that needle tube 210 has penetrated membrane 302 (not shown), taking suture end 405 through membrane 302 as well. In FIG. 8B, needle tube 210 is shown piercing three layers of tissue 902, 904, 906. Thus, eventually, the bite of suture 230 will include those layers. In FIG. 8C, suture passer 200 has been inserted still further into needle track 150, causing trigger 220 to be depressed, which, as described with reference to FIGS. 2A-2C, resets needle tube 210 to "off" and releases suture 230 from suture passer 200. FIG. 8D depicts a close-up of the device from FIG. 8C. In FIG. 8D, needle tube 210 and suture end 405 have penetrated membrane 302. Suture end 405 is seen to be free of hook 205 and needle tube 210. In FIG. 8E, suture passer 200 has been withdrawn from needle track 150. Suture end 405 has been retained—held by the retentive squeezing properties of membrane 302. FIG. 8F depicts the process being repeated with suture end 410, needle track 155, and membrane 305 (not shown). FIG. 8F also depicts the bite of the suture with suture ends 405, 410 each passing through tissue layers 902, 904, 906. And FIG. 8G depicts handle 100 after suture passer 200 has deployed suture ends 405, 410 into membranes 302, 305, respectively, and been withdrawn.

Figure 9A:
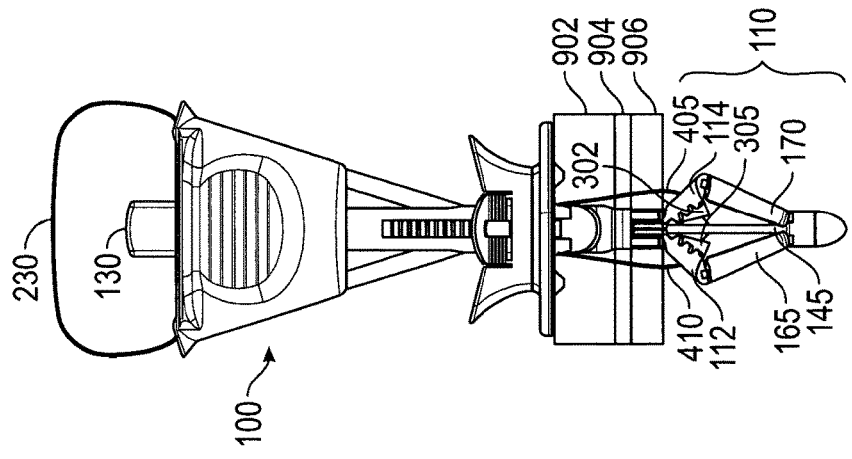

FIGS. 9A and 9B depict a handle 100 at different stages of capturing the suture ends. After suture ends 405, 410 are deployed onto membranes 302, 305 (as in FIG. 8G), control button 130 is pressed, moving control rod 145 distally to close catcher 110. FIG. 9A depicts handle 100 approximately mid-way through the process of capturing suture ends. As control button 130 is depressed, membranes 302, 305 fold between catcher elements 114, 314 (FIG. 3) and 112, 312 (FIG. 3), respectively, bringing suture ends 405, 410 with them. FIG. 9B depicts catcher 110 in the retracted configuration. Control button 130 has been fully depressed. In this configuration catcher 110 no longer provides a counterforce to the compressive forces of slider 115, which is still in the compressive position. That is, catcher 110 no longer presents a flat surface to tissue layers 902, 904, 906 and may be easily withdrawn. In the fully retracted position, elements 114, 314 and 112, 312 clamp respective suture ends 405, 410. Optional teeth 140, which may also be between catcher elements 112, 312 and 114, 314 (see FIGS. 6C, 8D) improve the hold on suture ends 405, 410.

FIGS. 10A and 10B depict an embodiment of a handle 100 automatically releasing the suture after catcher 110 has been fully retracted. In FIG. 10A, suture 230 has been deployed onto layers 902, 904, 906 of, for example, the abdomen wall with suture ends 405, 410 captured by catcher 110 on handle 100. Handle 100 has been pulled from surgical opening 1100, carrying with it suture ends 405, 410 and pulling more of suture 230 into surgical opening 1100 and through tissue layers 902, 904, 906. This has caused the loop of suture 230 to enter suture escape slot 400 (see FIGS. 4A-C). In FIG. 10B, continued pulling on handle 110 has caused the remainder of suture 230 to pass through suture escape slot 400 and out suture exit slot 160.

A method of using an embodiment to close a wound begins with the suture delivery device handle in the uncompressed and retracted configuration and the suture passer separated from the handle. In step 1, one hand removes a trocar from a wound. In step 2, the other hand inserts the handle into the trocar wound until the catcher is completely visible in a laparoscope image. In step 3, one finger presses the control button to open the catcher under visual guidance using the laparoscope image. In step 4, one hand holds the handle and the other hand pushes the slider toward the patient until the tissue to be sutured is firmly sandwiched between the slider and the catcher. The laparoscope image may be used to show whether the catcher is in contact with the peritoneum wall. In step 5, one hand holds the suture passer body and the other hand puts one end of suture into the hook of the suture passer. The finger then presses the needle button to load the suture passer. In step 6, one hand holds the handle and the other hand inserts the suture passer through the needle track until the trigger is actuated, releasing (or deploying) the suture on the catcher, again under the visual guidance of the laparoscope image. In step 7, steps 5 and 6 are repeated with the other end of the suture and the other needle track. In step 8, one finger presses the control button to capture the suture ends under visual guidance. In step 9, one hand pulls the handle from the wound and harvests from it the two suture ends.

Figure 11:
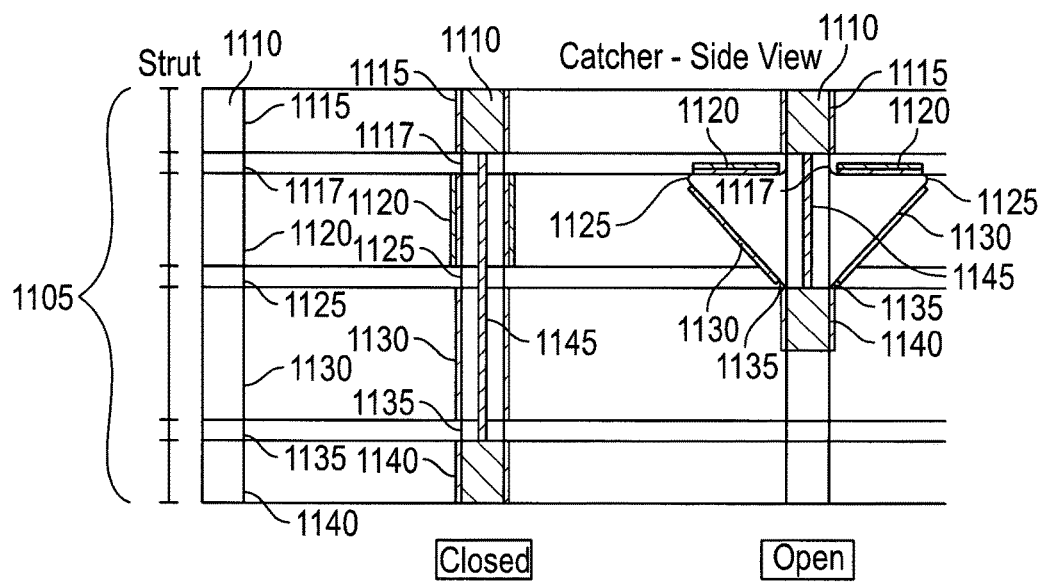
FIG. 11 depicts an embodiment of a suture catcher in cross-section.

FIG. 11 depicts an embodiment of struts from a suture catcher structure in a plan view and in cross-sections as part of an open and a closed suture catcher structure. Suture catcher 1105 may contain a number of struts 1110. Each strut 1110 may have a proximal connection part 1115 to a proximal joint 1117 (an upper hinge), an upper strut 1120, a middle hinge 1125, a lower strut 1130, a distal (or lower) hinge 1135, and a distal connection part 1140 to distal hinge 1135. The hinges may be living hinges, mechanical hinges, or metal wire/plate spring hinges. The struts may be made of metal (i.e. stainless steel), plastic (i.e. polypropylene, polycarbonate, polyurethane, nylon, or polyethylene) or any other suitable material. Multiple struts may be linked at the proximal joint as well as at the distal joint to form a catcher. A control rod 1145 may be coupled to the distal connection part 1140 of the catcher and extended to the proximal end of suture delivery device. In one embodiment, motion of control rod 1145 drives the up and down movement of distal connection part 1140 resulting in the opening (distal joint up, or "deploying") or the closing (distal joint down, or "retracting") of the suture catcher. In an alternate embodiment, the catcher deployment mechanism may be driven by controlling proximal connection part 1115. In embodiments, when in the deployed configuration catcher 1105 serves as a counterforce member to tissue-compressing forces.

The lengths of the lower and upper struts may be selected based on the desired size of the target area of catcher 1105, or based on the desired angle formed between the upper and lower struts, or both. The shape of the struts may be rectangular or trapezoid. An advantage of a trapezoidal shape over a rectangular shape is that a trapezoidal shape provides additional membrane packing space. The outer surface of the struts (the surface visible in the retracted configuration) has many possible variations including flat, flat with curved edges, or curved. Designs with curved surfaces may result in a suture delivery device with a more atraumatic outer profile, since there would be fewer sharp edges. That is, in the various embodiments, strut components (including protruding and matching features) may be flat or may be curved to create a more rounded exterior profile, see, e.g., FIG. 13C.

Figure 12A:
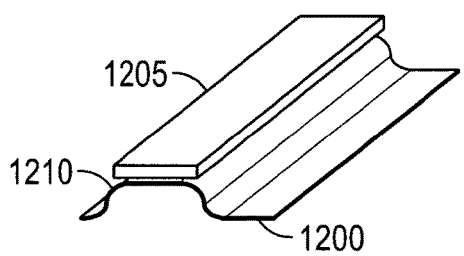
FIGS. 12A and 12B depict embodiments of attaching membranes to struts.
Figure 12B:
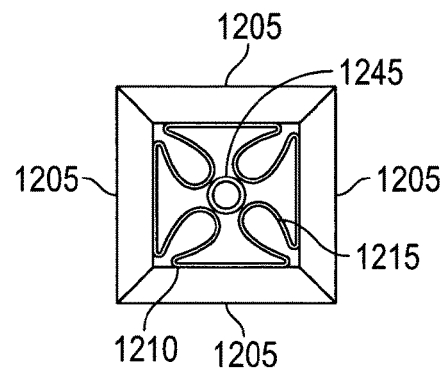

FIGS. 12A and 12B show embodiments of attaching a membrane 1200 to a strut 1205. Membrane 1200 may be made of materials such as polyurethane, PVC, polypropylene, or other pliable material that would not resist being punctured or folded too greatly. To retain a suture more reliably between struts during device withdrawal, the catcher should close so that adjacent struts (or features for securing a suture, such as teeth) can engage in the designed manner. Proper closure of the catcher is much more likely if the membrane folds and packs into a profile that does not interfere with catcher frame closure. But catcher membranes may not naturally fold or pack in any particular direction or configuration. In addition, the space where the membrane may be packed is the space enclosed by the struts when they are contracted, and that space is limited. Furthermore, membranes with varying thickness and stiffness have different folding behaviors. The membrane attachment position relative to the strut has been found to impact its folding behavior. Thus, in embodiments, the struts or frame of the catcher may be designed to guide the membrane to fold in a desired manner, e.g., radially inward toward control rod 1245 (FIG. 12B).

The membrane may be coupled to the frame struts by various methods (e.g., adhesive, mechanical attachment, etc.). The membrane attachment position may be fully extended to the edge of the strut or may be attached in recessed position from the strut's lateral edges. To facilitate full enclosure of membrane by the strut upon catcher closure, membrane 1200 may be attached in recessed position 1210 from the lateral edges as shown in FIGS. 12A and 12B. Membrane 1200 typically has a minimum curvature and radius. Thus, attaching membrane 1200 recessed from the edge of strut 1205 allows for membrane 1200 to fold within the space defined by the struts, as shown by fold 1215. This helps prevent membrane 1200 from clustering between struts 1205 and reducing their ability to clamp together and secure a suture.

Figure 13A:
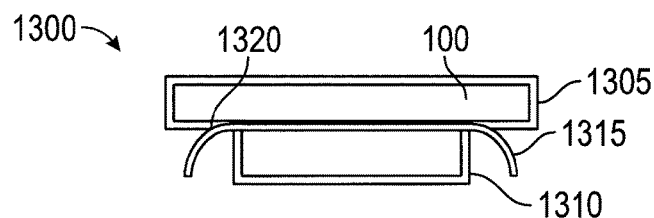
FIGS. 13A-13D depict embodiments of attaching membranes to struts.
Figure 13B:
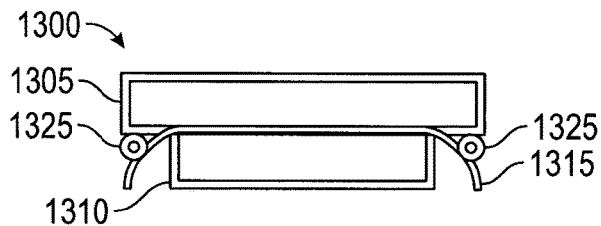

FIGS. 13A-13D depict further embodiments for attaching a membrane to a strut. In FIG. 13A, strut 1300 has a two-piece construction, comprising an outer (or top) strut component 1305 and an inner (or bottom) strut component 1310 that combine to sandwich membrane 1315. The outer strut component may be wider than the inner strut component and a membrane attachment edge 1320 may be recessed from the edges of the outer component 1305. The difference between outer and inner strut component widths provides membrane attachment support by sandwiching the membrane and facilitates membrane folding by allowing membrane attachment edge 1320 to be recessed from the edge of strut 1305. In FIG. 13B, a membrane guiding feature 1325 may be used between strut 1305 and membrane 1315 to help push the membrane inward. Guiding feature 1325 may be a part of strut 1305, or membrane 1315, or a separate add-on component. Guiding feature 1325 may be, for example, a metal rod. Guiding feature 1325 protrude from the surface of the strut to increase or initiate the folding of membrane 1315. Thus, instead of taking a path more in parallel with strut 1305, membrane 1315 bends immediately inwards to help achieve the intended membrane folding. Protruding features of various shapes and sizes may be used to create different membrane bending patterns as intended.

Figure 13C:
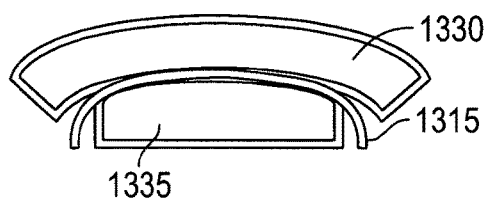
Figure 13D:
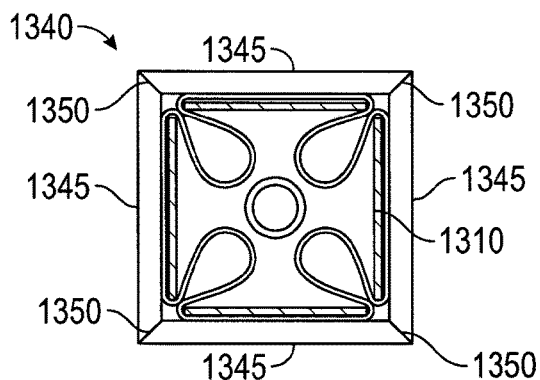

In FIG. 13C, outer strut component 1330 may have edges that curve inward slightly to help facilitate membrane 1315 folding inward and away from the outer strut edges as the catcher closes. FIG. 13D depicts an embodiment of a catcher with a 2-piece strut design in a closed configuration. Closed catcher 1340 also has an outer strut component 1345 with an angled edge 1350 that increases the contact surface between outer strut components 1345.

Generally, the membrane may be coupled to the catcher struts or frame using various methods, such as adhesive, mechanical attachment, fusing, injection molding, or any other suitable means.

Figure 14A:
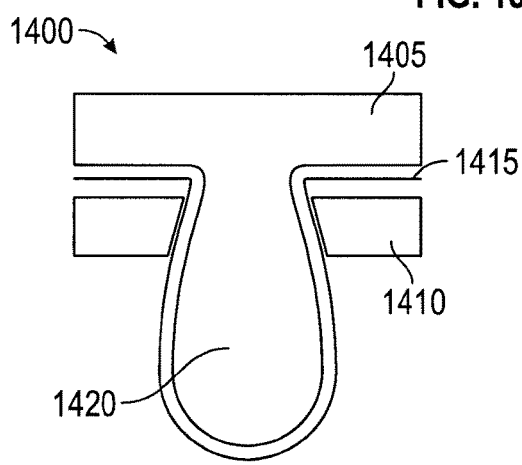
FIGS. 14A and 14B depict an embodiment for attaching a membrane to a strut.
Figure 14B:
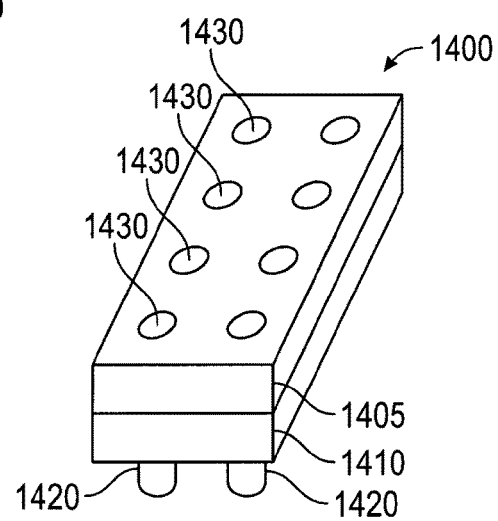

FIGS. 14A and 14B depict an embodiment for attaching a membrane mechanically. In the embodiment, strut 1400 may have a two-piece construction with an outer/top strut component 1405 and an inner/bottom strut component 1410 that sandwich membrane 1415. Membrane 1415 is preferably pliable and may be secured by mechanical means, such as clamping or clasping. In this embodiment, outer strut component 1405 and inner strut component 1410 have interlocking features 1420 that assemble together to secure membrane 1415. Interlocking features 1420 include a protruding feature and a corresponding hole, which cooperate to fix membrane 1415 between struts 1405, 1410. Membrane 1415 elongates and conforms around the protruding feature 1420. Positions 1430 indicate a possible pattern of features 1420. Alternately, membrane 1415 may have holes punched that correspond to features 1420, so that membrane 1415 does not elongate to conform to features 1420.

Figure 15A:
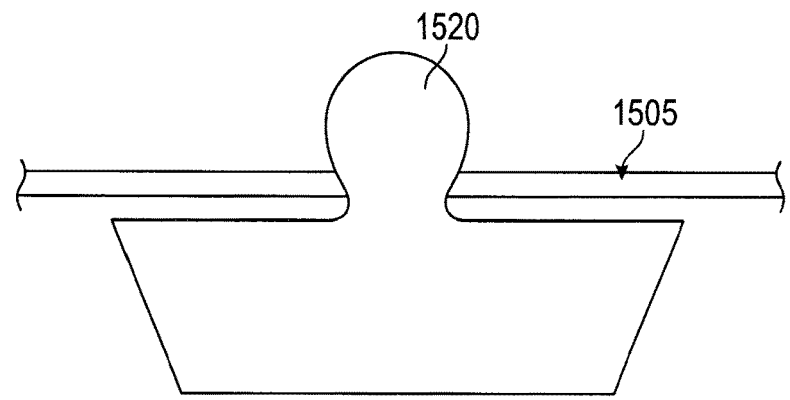
FIGS. 15A and 15B depict an embodiment for attaching a membrane to a strut.
Figure 15B:
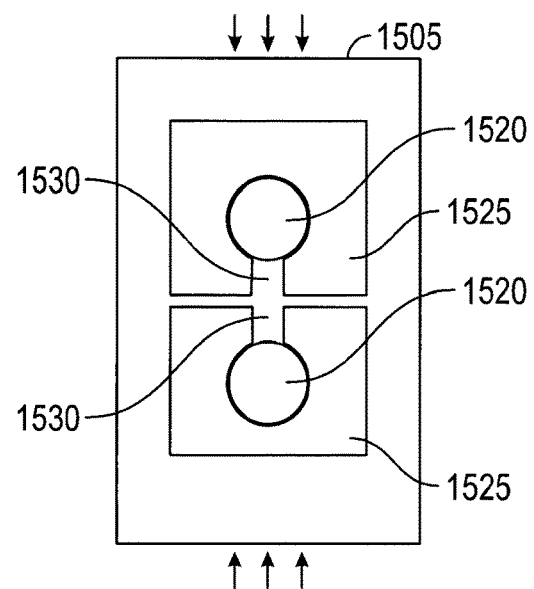

FIGS. 15A and 15B depict an embodiment for attaching a membrane mechanically. In FIG. 15A, membrane 1505 has holes that allow the passing of protruding feature 1520. Alternatively, the protruding feature may be designed to puncture through membrane 1505 during the strut component interlocking process. A strut may contain multiple protruding and matching features to form a desired securing pattern.

Membrane attachment to the strut may be provided solely by the mechanical force produced by the interlocking components. Alternatively, adhesive may also be used to provide additional membrane attachment force. In embodiments where the protruding features are plastic and pass through holes in the membrane, the protruding feature can be melted or welded to the other strut component to provide an interlocking force. Additionally, the membrane may also be heat fused to one or both of the strut components.

Metal has an advantage over plastic in resisting creep and it functions more effectively as a tension holding element. In an alternate to the embodiment of FIG. 15A, membrane 1505 may stretch over protruding feature 1520 while strut components with matching feature in the form of "metal clip" are applied to sandwich membrane 1505 to protruding feature 1520. The metal clip part may be created by stamping or by any other appropriate method.

FIG. 15B depicts an addition to the embodiment of FIG. 15A. The matching feature has the form of a thin metal part—a slide-lock 1525 with a slot 1530. Slot 1530 is sized to slide onto the neck of protruding feature 1520. In this variation, the membrane has punched out holes to admit the protruding features. Slide-lock 1525 may be stamped or laser cut or made by any other appropriate method.

Figure 16:
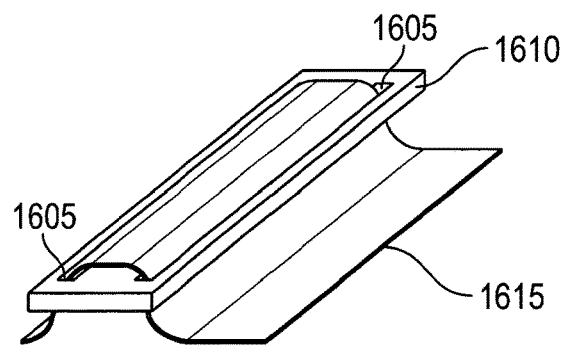
FIG. 16 depicts a perspective view of an embodiment for attaching a membrane to a strut.

FIG. 16 depicts an embodiment for attaching a membrane mechanically—by threading it through a strut. Small slits 1605 may be created in a suture catcher strut 1610 and a membrane 1615 may be threaded through these openings. The size, length, and geometry of the openings may be optimized to control the attachment of membrane 1615 to strut 1610. Membrane 1615 may be inserted through a first slit 1605 from the interior side of strut 1610, traverse the exterior side of strut 1610, and then be inserted through the second slit 1605 to re-emerge on the interior side of strut 1610. Additionally, adhesive or other methods may be used as adjunct methods to increase the membrane-strut fixation force. Slits 1605 also serve the purpose of guiding or controlling the angle at which membrane 1615 exits strut 1610. Slits 1605, since they are positioned away from the lateral edges, result in membrane 1615 emerging on the interior of the strut recessed some distance from the lateral edge. Membrane 1615 is therefore less likely to interfere with strut closure as it has room to turn radially inward and is already guided in that direction by the slits 1605.

In an alternate embodiment, slits 1605 may extend to one end of strut 1605, creating openings for membrane 1615 to be slid into and be retained by strut 1610 (akin to a paper clip). The opened edge may be on the outer radial edge or on the inner edge in proximity to the device shaft.

A membrane stretched between two struts has a tendency to sag along the unsupported edges. In embodiments, membranes may sag, particularly where they extend radially beyond a direct line between two struts ends. In such sections the membrane does not have sufficient support from the struts, and may not be stiff enough itself to resist bending away when contacted by a needle or suture passer. Such bending may reduce the effective target zone for suture capture, since the needle may slide past the bending membrane instead of penetrating it. Embodiments are directed to managing the extent the membrane may sag or bend, many by improving membrane tautness.

Figure 17:
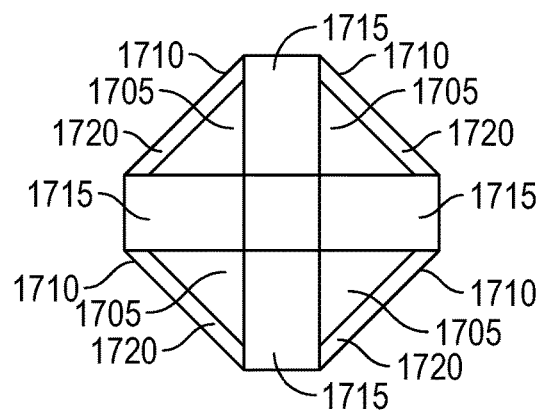
FIG. 17 depicts an embodiment for managing membrane sag.

FIG. 17 depicts an embodiment of a catcher for managing the extent the membrane may sag or bend. In FIG. 17, membranes 1705 have straight-line edges 1710 that follow a line between the external radial edges of two adjacent, opened struts 1715. Membranes 1705 may be more effective in capturing sutures than shapes where membrane material extends beyond the line between strut ends (e.g., membranes with extended arc shaped outer edges). Straight-line shaped membranes 1705 eliminate membrane areas that are not well-supported by struts 1715 and thereby reduce the likelihood of membrane 1705 bending upon needle contact. Thus, membranes 1705 maximize the effective suture capture area.

In an alternate embodiment, the membrane may be any shape, or non-existent, between struts where suture capture is not intended, i.e., where needle tracks are not directed.

In embodiments, the edge of membrane 1705 may be reinforced with a tension element 1720 that improve membrane tautness. In one embodiment, tension element 1720 may be a string or other fiber coupled to the edge of the membrane with its ends attached to the catcher struts, much like the string around the periphery of a kite. For example, tension element 1720 may be a Kevlar fiber fused at the edge of the membrane. The fiber may be stretched to create tension in the fiber section between the strut ends and thereby provide support to the outer edge of the membrane. A mechanism for tensioning the fiber may be the deployment of the catcher struts. An alternate or additional mechanism for tensioning the fiber may be to cause the struts to extend radially outward after the catcher struts have been deployed.

The fiber may be coupled to the membrane edge by different methods. One method is to glue the fiber to the edge of the membrane. Another method is to fold the membrane edge to create a pocket to contain the fiber. Yet another method is to fuse membrane layers together with the fiber embedded between the layers.

The tension element may be more pliable than the membrane so that the tension element does not adversely impact membrane packing. In embodiments, the tension element itself may have a default bend that assists the folding of the membrane. The cross-section of a tension element may be of any desired shape.

Figures 18A, 18B:
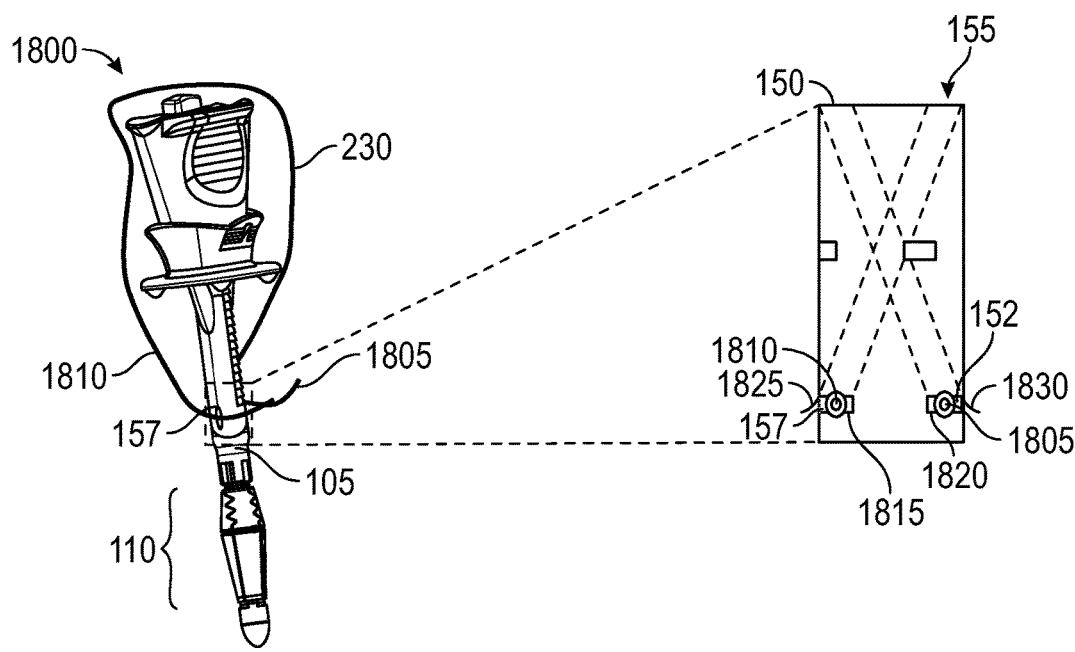
FIGS. 18A and 18B depict an embodiment of a suture delivery device handle.

FIGS. 18A and 18B depict an embodiment of a suture delivery device handle 1800. In embodiments, suture ends 1805, 1810 may be loaded onto handle 1800 before handle 1800 is inserted into inserting into the surgical opening. In FIG. 18A, suture ends 1805, 1810 have been loaded onto handle 1800 at the distal openings 152, 157 of needle tracks 150, 155. FIG. 18B depicts a friction method of loading a suture. In FIG. 18B, slots 1815, 1820 are configured to retain suture ends 1805, 1810, by, for example, a press-fit or other wedging action. In an alternate embodiment, flexible retaining flaps 1825, 1830 are added to further retain suture ends 1805, 1810. Flaps 1825, 1830 may be, for example, rubber or metal depending on the retention force desired. Furthermore, handle 1800 may have suture ends 1805, 1810 loaded during the factory assembly process.

Figure 19A:
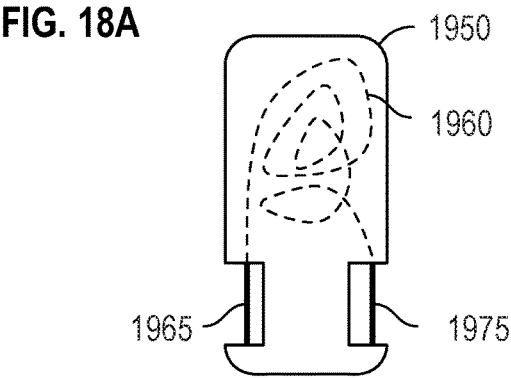
FIGS. 19A and 19B depict an embodiment of a suture delivery device handle.
Figure 19B:
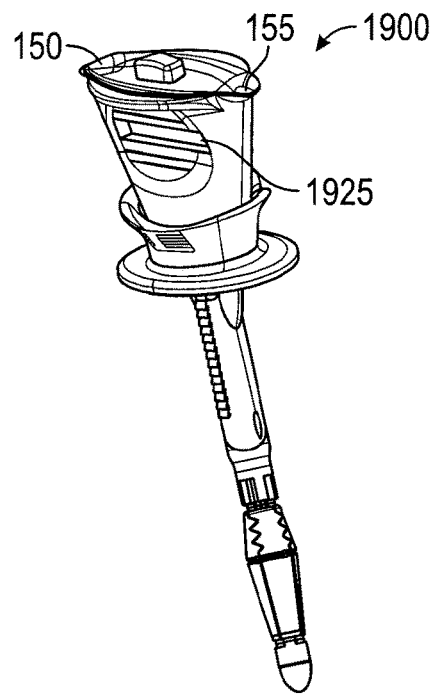

FIGS. 19A and 19B depict an embodiment for loading a suture using a suture cassette. In FIG. 19A, a cassette 1950 stores one suture 1960 and has two access ports providing access to suture ends 1965, 1975. In FIG. 19B, handle 1900 has a cassette insert port 1925 configured to receive suture cassette 1905 and position exposed suture ends 1965, 1975 within needle tracks 150, 155 internally within handle 1900 for eventual loading onto a suture passer in preparation for deploying the sutures.

In an embodiment, slider 115 is spring-loaded to compress the tissue to be sutured upon pressing control button 130. Thus, in the embodiment, pressing control button 130 may cause two actions. First, catcher 110 may be deployed, and second, slider 115 may be forced to move distally—toward catcher 115. These actions may be accomplished with a spring that is loaded as the slider moves proximally—away from catcher 110. The spring may have a trigger that is actuated by the final stage of the button stroke so that pressing control button 130 first opens catcher 110 and, as control button 130 is pressed an arbitrary further amount, the trigger actuates to release the spring, which then pushes slider 115 against the skin, sandwiching the tissue between slider 115 and catcher 110.

Figure 20A:
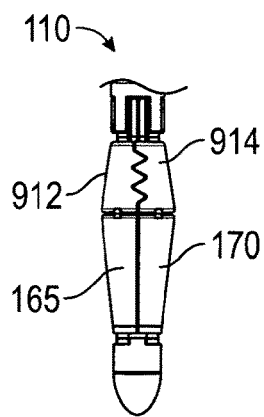
FIGS. 20A-20C depict an embodiment of a suture catcher.
Figure 20B:
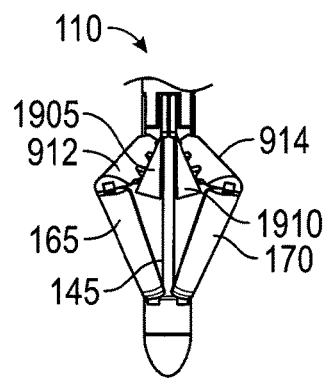
Figure 20C:
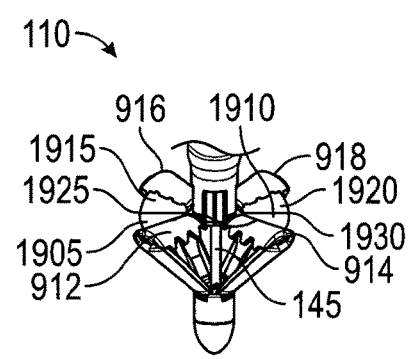

FIGS. 20A-20C depict an embodiment in which wings are flexible sections of catcher struts and assist with capturing a suture. FIG. 20A depicts struts 912, 914, 916, 918 with sections similar in dimension and stiffness to struts 112, 114, 312, 314 (FIG. 3). Struts 912, 914, 916, 918 have flexible wings 1905, 1910, 1915, 1920. FIG. 20B depicts flexible wings 1905, 1910 being folded within catcher 110 as it is retracted. When catcher 110 is deployed, wings 1905, 1910, 1915, 1920 open to their intended positions, and wing pairs 912, 916 and 914, 918 open and overlap, presenting a target area for a suture as in FIG. 20A. In the embodiment, the target area presented by the overlapping wing pairs is a plane similar to that presented by membranes 302, 305 (FIG. 3), yet 1905, 1910, 1915, 1920 do not rely on tension for support and, thus, they may be configured to extend beyond an area defined by struts 912, 914, 916, 918. Wings 1905, 1910, 1915, 1920 may assist capturing a suture end by being punctured, similarly to membranes 302, 305, or they may assist capturing a suture by allowing suture passer 200 to pass through seams 1925, 1930 between the wing pairs. Once suture passer 200 passes through seams 1925, 1930, releases the suture, and is withdrawn, the wing pair 1905, 1915 or 1910, 1920 closes about and captures the deployed suture. The captured suture ends may then be drawn in by the wing pair when catcher 110 is retracted (FIG. 20C) and more firmly grasped by the strut pair 912, 916 or 914, 918.

FIGS. 21A-21E depict embodiments allowing multiple uses of a catcher membrane by varying the location that a catcher membrane is penetrated. Generally, each insertion of needle through a membrane creates and leaves a footprint on the membrane. With multiple needle insertion, the holes created in the membrane may reduce the membrane's ability to capture and retain subsequent sutures. Embodiments provide for multiple uses of the same device by changing the area penetrated by the suture passer for each use. The suture catcher may be rotated so that the intended membrane area for needle penetration is (sufficiently) different every time. The rotation may be large angle or small angle depending on the intended number of needle penetrations and allowable repeated needle penetrations. Other embodiments reduce the probability of a needle penetrating in the same area repeatedly by, e.g., providing a random rotation of the suture catcher.

Figure 21E:
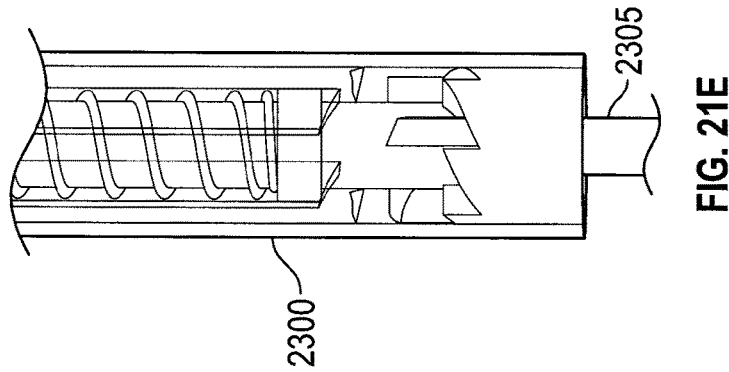
FIGS. 21A-21E depict embodiments of a multi-use suture catcher.
Figure 21B:
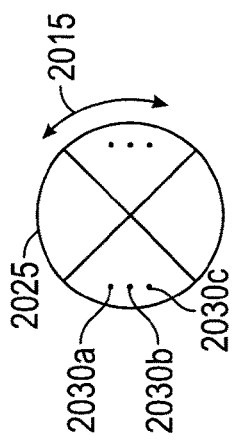
Figure 21D:
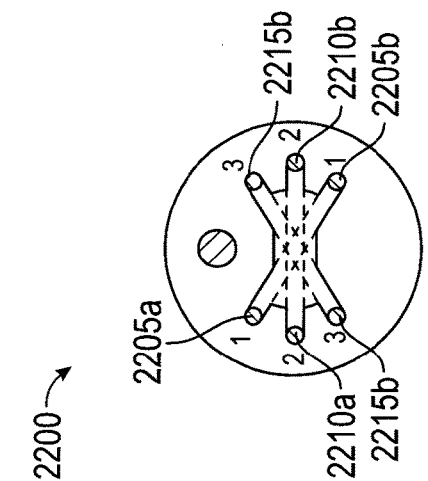
Figure 21A:
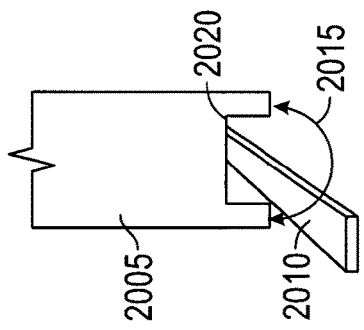

FIGS. 21A and 21B depict an embodiment of a multi-use catcher with a random rotation mechanism. In this embodiment, the struts of the catcher may pivot within a defined distance relative to the handle shaft. A membrane attached to the struts may pivot with them. In FIG. 21A, a single strut 2010 is pictured for clarity, but the following description applies to the other struts of a catcher. Catcher strut 2010 is free to pivot about an angle 2015 within a window 2020 in shaft 2005. The size of window 2020 may define how much catcher strut 2010 can rotate. Window 2020 may be provided in a proximal part (e.g., proximal connection part 1115 (FIG. 11) for each strut of a catcher, allowing each individual strut to move freely within the windows. The connection between the distal joint and the control rod may be floating such that rotation of the proximal joint will result in rotation of the whole catcher. The random rotation of the catcher allowed in this embodiment reduces the probability that two needles will penetrate the membrane precisely at the same location. FIG. 21B depicts a puncture pattern on a membrane that may result from the rotation of a catcher equipped with struts as in FIG. 21A. In FIG. 21B, membrane 2025 shows punctures 2030*a*, 2030*b*, 2030*c* that may result from the use of suture passer within a single needle track, e.g., needle track 155 (FIG. 3), as the catcher and membrane are rotated within angle 2015.

Figure 21C:
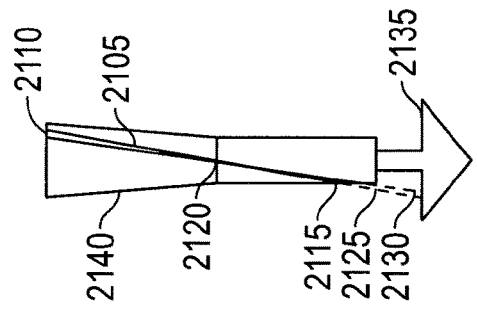

FIG. 21C depicts an embodiment of a multi-use catcher with a needle track with an internal pivot point. Needle track 2105 may be greater in diameter than a needle or suture passer between insertion point 2110 and a narrowing 2120 and between an exit point 2115 and the narrowing 2120. Narrowing 2120 may be a constriction of needle track 2105, or simply a bump, at some position within needle track 2105 that functions as a pivot point. With the needle or suture passer being able to move radially within needle track 2105, narrowing 2120 may function as a pivot point to facilitate moving the distal end of the needle or suture passer with respect to the surface of a suture catcher 2135 by moving the proximal end of the needle or suture passer, as depicted by exemplary suture passer positions 2125, 2130. Suture passer positions 2125, 2130 show that, per the embodiment, a suture passer may exit needle track 2105 at various angles relative to shaft 2140 and suture catcher 2135. The changing angles reduce the probability that the needle will penetrate a membrane on suture catcher 2135 at precisely at the same location. In an embodiment, needle track 2105 may be hourglass shaped. In a further embodiment, needle track 2105 may not have narrowing 2120, but still allow for exemplary suture passer positions 2125, 2130 by being generally larger in diameter than the needle or suture passer.

FIG. 21D depicts a top view of a handle 2200 that provides for multiple uses of a catcher membrane. In FIG. 21D, multiple needle track pairs 2205*a* and *b*, 2210*a* and *b*, and 2215*a* and *b*, each target different respective areas (not shown) of a membrane. In addition, a dial feature (not shown) may rotate atop handle 2200 to expose one set of needle tracks at a time.

FIG. 21E depicts a cross-section of a multi-use embodiment employing an automatic pen rotation mechanism. Rotation of the suture catcher may ensure that a needle or suture passer penetrates a membrane at an unused location of the membrane. In the embodiment, an automatic pen rotation mechanism 2300, or a variation, may be used to achieve this. Mechanism 2300 contains features that transfer up and down movement of control rod 2305 into a rotational movement of control rod 2305. With control rod 2305 connected to the distal joint of the suture catcher so that rotation of control rod 2305 results in rotation of the distal joint, and with the proximal joint of the suture catcher allowing rotational movement of the suture catcher, the rotation of control rod 2305 will result in the rotation of the suture catcher. The magnitude of the resulting rotation is controlled per the design of rotation mechanism 2300 and may be arbitrarily small or large. In a variation of this embodiment, the up and down movement of control rod 2305 results in a rotational movement of the proximal joint of the suture catcher, the connection between the distal joint and the control rod is floating, and the rotation of the proximal joint results in the rotation of the whole suture catcher.

Embodiments may employ a suture passer with a tip designed to receive sutures that are pre-loaded on the handle (see, e.g., FIGS. 18A and 18B and related text regarding loading sutures on the handle). In such embodiments, the tip of the suture passer preferably is able to: grasp the suture ends before entering the abdominal tissues; retain the suture ends while penetrating the tissue to be sutured and a catcher membrane, if the catcher is so equipped; and deploy the suture ends.

FIGS. 22A-22D depict different embodiments of suture passers designed to grasp, retain, and deploy a suture. In FIG. 22A, suture passer 2400 has a fixed tip 2405 with a slot 2410 configured to engage a suture 2415 positioned at an exit 2420 of a needle track 2425. In FIG. 22B, suture passer 2430 has an actuated tip 2435 with a clamping member 2440 for clamping a suture 2445 against a fixed member 2450 at the urging of an apparatus 2455, e.g., a driving axle, internal to suture passer 2430. In FIG. 22C, suture passer 2460 has a grasping tip 2465 with a needle head 2470 actuated by an internal rod 2475 for grasping a suture 2480 against a needle tube 2485. FIG. 22D depicts the grasping tip of suture passer 200 previously described with reference to FIGS. 2A and 2B for comparison. This embodiment of a suture passer may also be used to receive sutures that are pre-loaded on the handle. Similarly, the embodiments of suture passers in FIGS. 22A-22C may be loaded with a suture before being inserted into a needle track of a handle. In embodiments, any of the needle tip embodiments disclosed may be configured to cooperate with any of the needle tracks disclosed.

In an embodiment of a procedure for deploying a suture loaded on a handle, after the tissue to be sutured is sandwiched by a handle (see, e.g., FIG. 8B), the suture passer is inserted into and through the needle track until the tip reaches the suture loaded on the handle. The suture is then loaded onto the suture passer. Then the suture passer is inserted through the needle track to deploy the suture end on the catcher. Depending on the catcher configuration, the suture end may be deployed by being released within grasping distance of catcher struts, or may be deployed by being inserted into a catcher membrane and then released. After the suture is released, the suture passer may be withdrawn and inserted into a second needle track with the above procedure repeated with a second suture loaded on the handle.

Figure 23A:
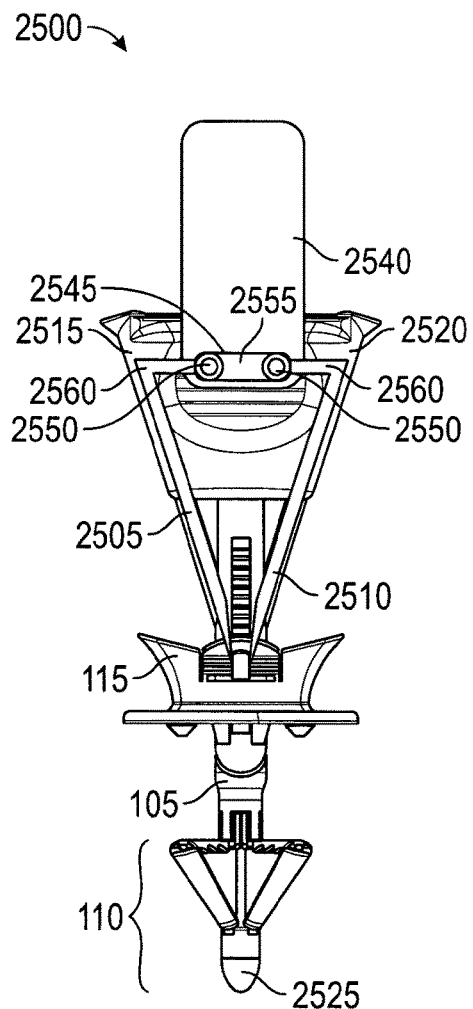
FIGS. 23A and 23B depict an embodiment of a suture delivery device.
Figure 23B:
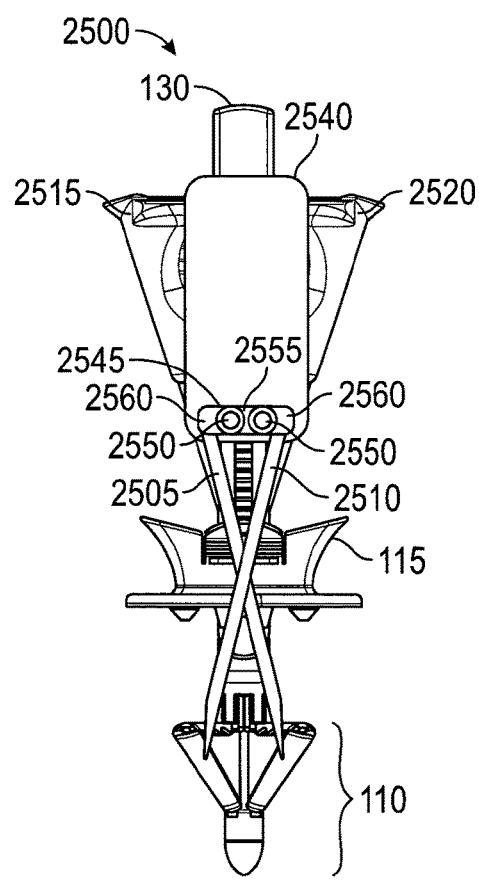

FIGS. 23A and 23B depict a cross-section of an embodiment in which suture passers are integrated into a handle 2500. In FIG. 23A suture passers 2505, 2510 are situated within needle tracks 2515, 2520, respectively, and used to deploy sutures. Suture passers 2505, 2510 may be designed to reside within needle tracks 2515, 2520. Control button 2540 (or control lever, or control slider) may, upon actuation, cause suture passers 2505, 2510 to travel through needle tracks 2515, 2520, grasp the loaded sutures, extend from shaft 105 of handle 2500, and penetrate the tissue to be sutured, e.g., the abdominal tissues. Suture passers 2505, 2510 may then deploy the suture onto catcher 110.

In the embodiment, suture passers 2505, 2510 may be deployed using a roller and track 2545 and control button 2540 to advance the two suture passers through needle tracks 2515, 2520 to deploy the sutures. Roller and track 2545 may include rollers 2550 within a track 2555 connected to actuating arms 2560. Control button 2540 when pressed may cause roller and track 2545 and actuating arms 2560 to travel toward a distal end 2525 of handle 2500. Actuating arms 2560 then force suture passers 2505, 2510 through needle tracks 2515, 2520 to deploy the sutures. Roller and track 2545 are configured to allow actuating arms 2560 to move inwardly within handle 2500 as arms 2560 travel in the distal direction. In FIG. 23B, control button 2540 has been completely depressed, forcing suture passers 2505, 2510 to extend past catcher 110, open suture passer tips (see, e.g., FIGS. 22B-D), and deposit the sutures (not shown). The motion of control button 2540 has revealed control button 130, which as described earlier controls catcher 110 and perhaps also slider 115. The motion has also caused rollers 2550 to move inwardly within track 2555 in response to actuating arms 2560 following the contour of needle tracks 2515, 2520. In an embodiment, the functions of control buttons 130 and 2540 are performed by a single control button.

The embodiments of the suture delivery devices may be used to practice the methods for inserting and withdrawing a suture passer, and for capturing, retaining, and securing a suture. In embodiments, membrane properties influence capturing, retaining, and securing a suture. As described, when a needle or suture passer carrying a suture is inserted through a membrane, a suture may be released and captured by the membrane. When the catcher is then closed, the membrane may fold with the catcher frame closure, retaining the suture within the membrane. The membrane itself may be made of a material with a high coefficient of friction or further having designs that increase the suture-retaining properties of the membrane. The retentive property may be a function of the material thickness, or of the number of material layers, or of the material surface. The retentive property may be on either or both sides of the retaining surface.

In embodiments, a suture may be secured by catcher strut edges. A number of methods may be employed (separately or in combination) to ensure that a suture is secured to the distal end of the device. Mechanical clamping of the suture may be used to retain the suture during the withdrawal of the suture delivery device from the surgical opening. Edges of adjacent struts may be used to hold a suture securely (as a mechanical clamp). For embodiments in which a suture catcher is equipped with a membrane, the membrane retention force may not be sufficient to withstand the force exerted by the sutured tissue on the suture, even if the suture is properly engaged with the membrane. Thus, adjacent catcher struts may be used as a clamp to secure a suture. Such adjacent struts may be used independently (e.g., in catcher embodiments that do not include a membrane), or may be used in combination with a membrane (e.g., in catcher embodiments that include a membrane).

Figure 24A:
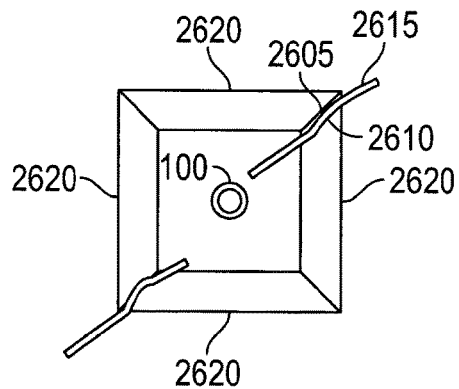
FIGS. 24A-24E depict embodiments of a suture catcher.
Figure 24B:
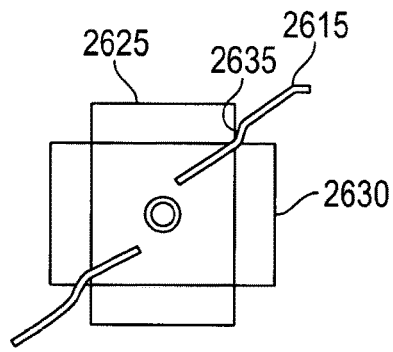
Figure 24C:
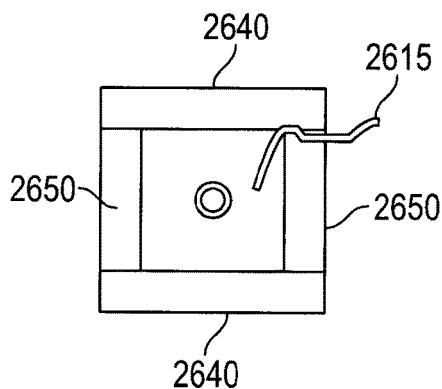
Figure 24D:
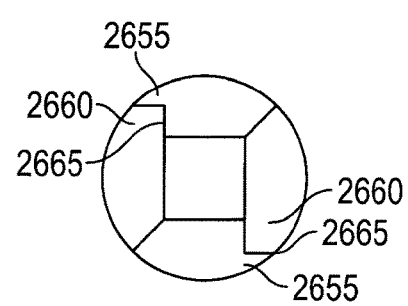
Figure 24E:
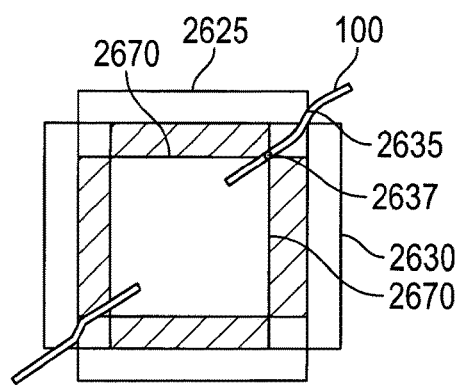

FIGS. 24A-24E depict embodiments of catchers that vary the length of a clamping surface, or the number of clamping surfaces, or number of contact points. In FIG. 24A, strut edges 2605, 2610 of struts 2620 have been angled to increase the contact surface with suture 2615. That is, the edges of catcher frame struts have been beveled and the suture is in contact with the strut for the length of the beveled edges. In FIG. 24B, struts 2625, 2630 are configured to create a single contact point 2635 against suture 2615. In FIG. 24C, struts 2640 are sized differently from struts 2650. Suture 2615 is clamped between the surfaces of a pair of differently sized struts 2640, 2650. In FIG. 24D, strut edges 2655, 2660 engage, creating an angle in suture contact surface 2665. The angle may be, e.g., 90 degrees. The catcher struts may also have saw tooth or wavy edges along the suture contacting edges. The advantage of designs with such edges is that the direction of the force applied to the suture is changed, increasing the normal force at points along the suture. In FIG. 24E, struts 2670 are added to the configuration of FIG. 24B, creating additional suture contact points 2637.

In embodiments, in addition to various strut designs just discussed, the strut edges may be roughened, treated, coated, or otherwise processed to increase friction and enhance suture-securing performance. For example, rubber pads or strips, or a rubber coating may be applied to the strut edges.

In alternate embodiments of a catcher, the suture may be clamped between a catcher strut folding inwardly against the control rod, or against a block positioned about the control rod that presents a flat surface to the strut as the strut folds inward. In such embodiments, both the membrane and the suture may be clamped between an exterior element (the strut) and an interior element (either the control rod, or the block about the control rod). Since the effectiveness of clamping a suture may be associated with the sufficient (or complete) closure of the suture catcher, the level of the applied closing force and any interference caused by the membrane may affect clamping effectiveness.

In the various embodiments of a suture catcher, increasing the strut closing force may increase the retaining force on the suture. As a result, the catcher may retain the suture during a more forcible extraction of the suture delivery device from a surgical opening.

In embodiments, the suture may be retained by the catcher without a capture surface, e.g., a membrane. In such embodiments, the struts of the catcher may directly clamp the suture. The clamping action may, for example, be a part of the catcher being retracted for extraction from the surgical opening.

Figure 25A:
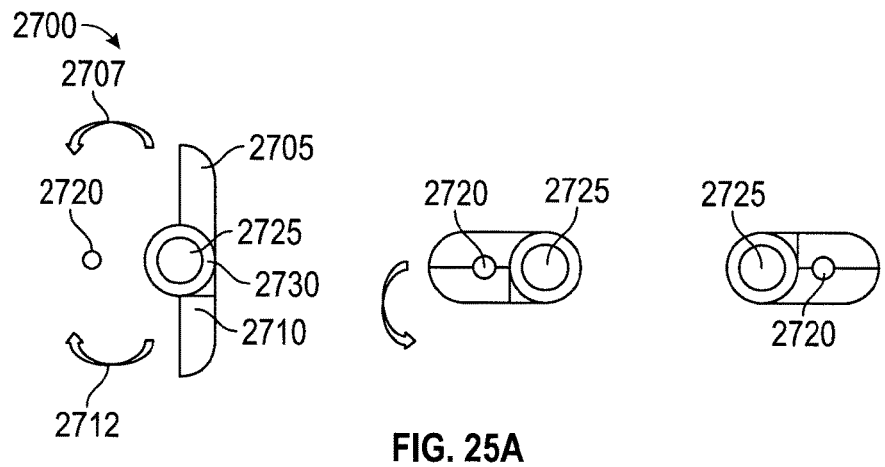
FIGS. 25A and 25B depict an embodiment of a suture catcher.
Figure 25B:
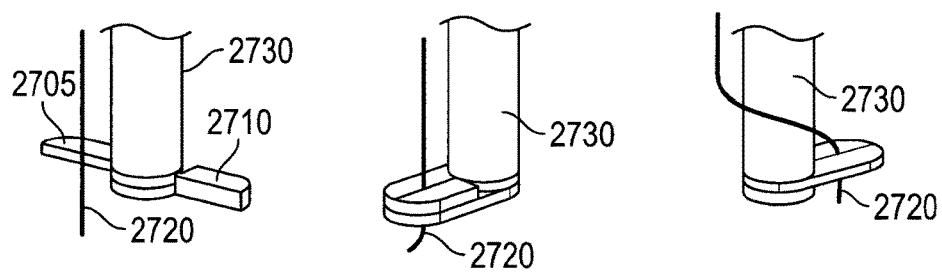
Figure 26:
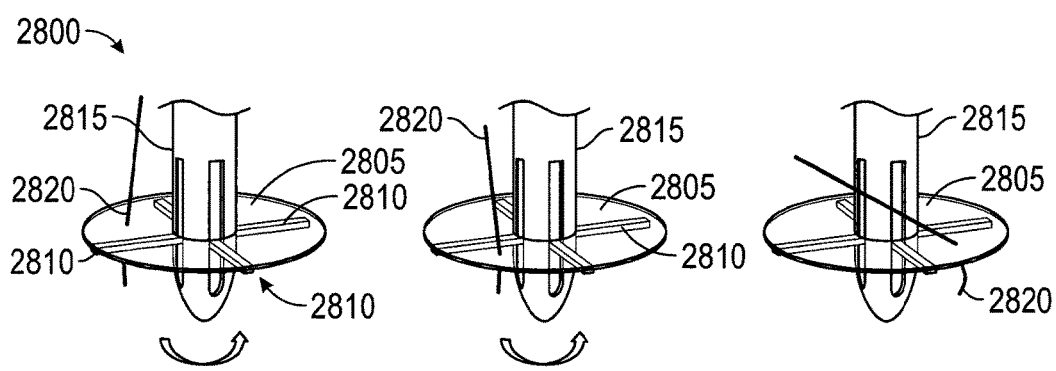
FIG. 26 depicts an embodiment of a suture catcher.
Figure 27:
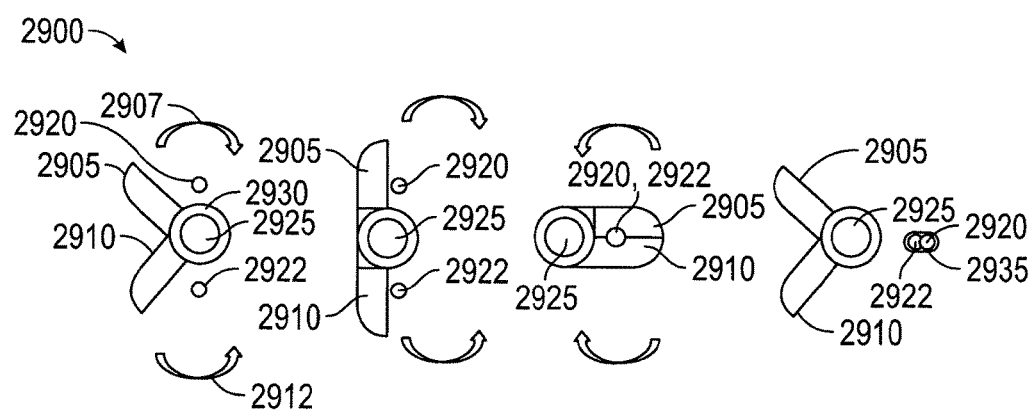
FIG. 27 depicts an embodiment of a suture catcher.

FIGS. 25-27 depict further embodiments for delivering and catching a suture. FIGS. 25A, 25B, and 26 depict embodiments for capturing a suture on one side of a surgical opening and moving the suture to the other side for completing the suture. FIGS. 25A and 25B depict top and perspective views, respectively, of a clamping apparatus 2700 with clamping arms 2705, 2710 that pivot in directions 2707, 2712, respectively, to capture a suture end 2720. Clamping arm 2705 may be rotated by inner shaft 2725 and clamping arm 2710 may be rotated by outer shaft 2730. Clamping apparatus 2700 may be substituted for catcher 110 on handle 100 of, e.g., FIGS. 1A and 1B. Clamping apparatus 2700 may be used to capture suture 2720 and position on an opposite side of clamping apparatus 2700 within a surgical opening.

FIG. 26 depicts a perspective view of a capture apparatus 2800 with a large area membrane 2805 supported by struts 2810 that pivot about a shaft 2815 to deposit a captured suture 2820 on an opposite side of capture apparatus 2800. Suture 2820 may be captured by membrane 2805 as discussed previously. Capture apparatus 2800 may also be substituted for catcher 110 on handle 100 of; e.g., FIGS. 1A and 1B.

An embodiment may include an umbrella-shaped membrane, where the membrane is supported by several radially expanding struts and spans 360 degrees around the device. Like an umbrella, the membrane may be in tension, making it easier for a needle to penetrate the membrane material. Also, the friction between the membrane material and the suture may be enough to disengage and retain the suture as the suture passer is withdrawn. Alternate embodiments may include multi-layer membranes where each layer has different orientation. In such a multi-layer membrane, the suture may be disengaged from the suture passer due to both friction and becoming entangled in the lattice structure.

The embodiments depicted by FIGS. 25A, 25B, and 26, may be used according to the following method. The needle (or suture passer) carrying a suture is inserted into a needle track and then into the muscle/fascia layers on one-side of trocar wound using a handle equipped with either clamping apparatus 2700 or capture apparatus 2800. The suture passer releases the suture and is withdrawn. For clamping apparatus 2700, the suture is then captured by the motion of clamping arms 2705, 2710. For capture apparatus 2800, the suture has penetrated membrane 2805, which has material properties or designs to disengage the suture from the needle passer and retain it. Once the suture is retained, the suture may be moved by rotating apparatus 2700 or 2800 causing suture 2720 or 2820 to be repositioned to the opposite side of the trocar wound. The surgeon may then easily retrieve the suture, since the suture is positioned at the target point of a needle (or suture passer) inserted through the other needle track of the handle and through the tissue to be sutured. Once through the tissue to be sutured the needle (or suture passer) may capture the repositioned suture with guidance from a laparoscopic image. The captured suture may have a controlled shape, orientation, and tension that would facilitate the surgeon retrieving it. These embodiments, like previous embodiments, remove the need for an assistant to help move the suture to where the surgeon can grasp the suture with suture passer.

FIG. 27 depicts a top view of an embodiment for linking suture ends within a surgical opening. In FIG. 27, clamping apparatus 2900 has clamping arms 2905, 2910 that pivot in directions 2907, 2912, respectively, to sweep through an arc and capture suture ends 2920, 2922. Clamping arm 2905 may be rotated by inner shaft 2925 and clamping arm 2910 may be rotated by outer shaft 2930 (alternately, only one clamping arm is rotated to capture both suture ends). Clamping apparatus 2900 may be substituted for catcher 110 on handle 100 of, e.g., FIGS. 1A and 1B. Clamping apparatus 2900 may be used to capture suture ends 2920, 2922 and link them together with a link element 2935. Link element 2935 may be a crimp or biodegradable member affixed to one of clamping arms 2905, 2910. It may also be a clamp or clip. Additionally, suture ends 2920, 2922 may be linked using adhesive or heat, etc. The resulting suture linkage should be at least strong enough to sustain pulling the suture joint through the tissue track created by the needle or suture passer. Alternately, the suture linkage should be strong enough to provide wound closure.

Clamping apparatus 2900 may be used according to the following method. The sweepers or clamp arms are initially positioned not to interfere with suture delivery. Two suture ends are delivered on opposite sides of a trocar wound. The clamp arms are then rotated to bring the suture ends into contact with the link element. The suture ends and the link element are then pressed together by the clamp arms to link the suture. The suture delivery device may then be withdrawn.

With this embodiment, one option for finishing a suture involves delivering two ends of one suture. Once the two sutures ends are linked, the linked suture becomes a loop. The user may cut the suture at the proximal end—outside of the trocar wound. Then the user may pull the external suture ends to close the wound, and then knot the ends. Alternatively, the user could pull the suture link out through the surgical opening with the suture delivery device, or tug on one side of the suture loop to bring the link out through the tissue track created by the initial needle insertion. The user may then cut the suture joint, close the surgical opening and tie the knot. Another option is to deliver two suture ends into the abdomen, each end from a separate suture. Once the two sutures ends are linked, the user could withdraw the device and finish the suture as described above.

In an embodiment, a catcher closure mechanism is slider activated. A suture delivery device may have a sliding member, which can be positioned to sandwich abdominal wall tissue against a counterforce member (e.g., a catcher), in the abdominal cavity. Many of the embodiments described are configured this way. In this embodiment, the sliding member may be coupled to the catcher deployment mechanism so that movement of sliding member may be used to control the catcher opening and closing. With the sliding member coupled to the deployment mechanism, as the sliding member moves downward (towards the distal end of device), the catcher deployment mechanism may be actuated to open the catcher. When the sliding member moves upward (towards the proximal end of the device), the catcher deployment mechanism may be actuated to close the catcher. The position where the sliding member interacts with the catcher deployment mechanism may be designed as desired. In one embodiment, the catcher may be opened when the sliding member travels a small distance downward while the catcher may be closed when the sliding member travels a small distance upward. For example, moving the slider downwards may cause the distal joint to move upwards and thereby deploy the suture catcher. Various mechanism options may be used to enable this concept.

A method for using an embodiment may include: inserting a suture delivery device through a tissue track until a distal end is inside a cavity; moving a sliding member towards a device distal end to open a catcher and then sandwich the abdominal wall tissue between the catcher and the sliding member; delivering a suture to the suture retention element (catcher) by inserting a suture-carrying needle into the device until suture is released and retained at the distal end (or until the suture is released and captured by the catcher); moving the sliding member towards the proximal end of device to close the catcher and release the abdominal wall tissue; and withdrawing the suture delivery device from the cavity with the suture ends retained at the device's distal end.

A method for automatically deploying a suture may include: inserting a suture delivery device into a surgical opening; sandwiching the wound tissue; deploying the suture ends, and withdrawing the handle. Sandwiching the wound tissue may further include: pressing a button that causes the catcher to open and the slider to compress the tissue against the catcher. Deploying the suture ends may further include: using an independent suture passer, or using a suture passer that is integrated with the handle. Withdrawing the handle may further include: closing the catcher to capture sutures, and an automatic suture release.

A method for deploying a suture may include: loading a suture onto a handle, or loading a suture cassette into a handle; with a left hand, removing a trocar; with a right hand, inserting the handle into the trocar wound until the catcher is completely visible from a laparoscope image; with the right hand, releasing a control button that opens the catcher and then pushes the slider down to sandwich the tissue under visual guidance. The laparoscope image may be used to show whether the catcher is in contact with the peritoneum wall. In an embodiment, this method for deploying a suture optionally includes: with the left hand, holding the handle; with the right hand, inserting the suture passer through the needle track to deploy suture on the catcher under visual guidance; and repeating this with the other needle track under visual guidance. In another embodiment, this method for deploying a suture optionally includes: using the left hand, holding the handle; using the right hand, pushing a deployment button to deploy a suture on the catcher under visual guidance; using the left thumb, pressing the control button to capture the sutures under visual guidance; and using the left hand, pulling out the handle and harvesting the two suture ends.

Described herein are certain exemplary embodiments. However, one skilled in the art that pertains to the present embodiments will understand that the principles of this disclosure can be extended easily with appropriate modifications to other applications.

What is claimed is:

1. A suture delivery device for suturing tissue comprising:
   an elongated deployment member;
   a counterforce member disposed towards a distal end of the elongated deployment member, wherein the counterforce member is configured to transition between a retracted configuration that facilitates the counterforce member entering an incision and a deployed configuration that resists extracting the counterforce member from an incision;
   a compression member disposed towards a proximal end of the elongated deployment member with respect to the counterforce member, wherein the compression member is configured to resist entering an incision, and wherein the compression member and the counterforce member transitions between a compressed configuration and an uncompressed configuration;
   a suture catcher disposed towards the distal end of the elongated deployment member, wherein the suture catcher is configured to transition between a retracted configuration that facilitates the suture catcher entering an incision and a deployed configuration that facilitates catching a suture;
   a first needle track extending through the compression member and oriented to direct a needle advanced through the first needle track into engagement with a first area of the suture catcher when in the deployed configuration; and
   a second needle track extending through the compression member and oriented to direct a needle advanced through the second needle track into engagement with a second area of the suture catcher when in the deployed configuration, wherein the first area of the suture catcher when in the deployed configuration and the second area of the suture catcher when in the deployed configuration are situated on the suture catcher to allow their placement on opposite sides of an incision.

2. The suture delivery device of claim 1, wherein in the compressed configuration the compression member is at a first distance from the counterforce member and in the uncompressed configuration the compression member is at a second distance from the counterforce member, the first distance being less than the second distance.

3. The suture delivery device of claim 2, wherein the compression member is moved in transitioning between the compressed configuration and the uncompressed configuration.

4. The suture delivery device of claim 2, wherein the counterforce member is moved in transitioning between the compressed configuration and the uncompressed configuration.

5. The suture delivery device of claim 1, wherein the suture catcher comprises a membrane that retains a suture inserted into or through the membrane.

6. The suture delivery device of claim 1, wherein the suture catcher comprises struts configured to close about a suture, and wherein the first area of the deployed suture catcher comprises a first area between the struts and the second area of the deployed suture catcher comprises a second area between the struts.

7. The suture delivery device of claim 6, wherein the struts are provided with teeth that engage the suture upon the strut closing about the suture.

8. The suture delivery device of claim 6, wherein the suture catcher further comprises a membrane, the membrane and the struts being configured to position the membrane in the first and second areas between the struts, the membrane retaining a suture inserted into or through the membrane.

9. The suture delivery device of claim 1, wherein the suture catcher comprises struts, each strut with an attached flexible wing, wherein the first area of the deployed suture catcher comprises a first area between a first strut and a second strut, and the second area of the deployed suture catcher comprises a second area between a third strut and a fourth strut, wherein when the suture catcher is deployed the wings of the first and second struts unfold to position themselves in the first area between the struts and the wings of the third and fourth struts unfold to position themselves in the second area between the struts, wherein the wings in the first area are configured to retain a suture between them and the wings in the second area are configured to retain a suture between them, and wherein the first and second struts are configured to close about a suture retained by the wings of the first and second struts and the third and fourth struts are configured to close about a suture retained by the wings of the third and fourth struts.

10. The suture delivery device of claim 1, wherein the first and second needle tracks are integrated into the elongated deployment member and exit the elongated deployment member proximally from the counterforce member.

11. The suture delivery device of claim 10, wherein the first and second needle tracks are joined by a suture exit slot configured to allow a suture loop to exit the device.

12. The suture delivery device of claim 1, wherein:
the compression member is configured to move axially along the elongated deployment member in transitioning between the uncompressed and compressed configurations,
the first and second needle tracks each pass through both the compression member and the elongated deployment member,
the first and second needle tracks comprise respective first and second pairs of telescoping tubes, a first tube of each telescoping pair anchored at the compression member and a second tube of each telescoping pair anchored at the elongated deployment member to allow for angular changes,
motion of the compression member along the elongated deployment member results in the telescoping pairs of tubes varying an angle of the first needle track with respect to the elongated deployment member and an angle of the second needle track with respect to the elongated deployment member, the varying of the angles between the first and second needle tracks and the elongated deployment member resulting in varying the first and second areas of the suture catcher.

13. The suture delivery device of claim 1, further comprising a suture passer, the suture passer comprising:
a needle tube dimensioned to be accepted within the first or second needle track;
a shaft disposed within the needle tube, the shaft having a ramp on a distal end, the ramp, shaft, and needle tube configured to retain a suture when the ramp is at least partially covered by the needle tube and to release a suture when the ramp is not covered by the needle tube; and a trigger, the trigger causing, when moved in a proximal direction, the ramp to be uncovered, wherein the first and second needle tracks, needle tube, shaft, and trigger are configured to uncover the ramp when the suture passer is inserted a pre-determined distance into the first or the second needle track, and wherein the pre-determined distance positions the suture for capture by the suture catcher.

14. The suture delivery device of claim 1 wherein the first needle track and the second needle track each have a constriction between their proximal and distal ends, the constriction providing a point about which a suture passer in the first or second needle track may pivot and thereby vary the locations of the first and second areas of the suture catcher when in the deployed configuration.

15. The suture delivery device of claim 1 further comprising:
a suture cassette provisioned with at least one suture; and
a suture cassette port intersecting the first and the second needle tracks, wherein the suture cassette and the suture cassette port are configured to position a first suture end within the first needle track and a second suture end within the second needle track.

16. The suture delivery device of claim 1, further comprising:
a third needle track associated with the elongated deployment member and disposed to direct a third suture end towards a third area of the suture catcher when in the deployed configuration; and
a fourth needle track associated with the elongated deployment member and disposed to direct a fourth suture end towards a fourth area of the suture catcher when in the deployed configuration, wherein the third area of the suture catcher when in the deployed configuration and the fourth area of the suture catcher when in the deployed configuration are situated on the suture catcher to allow their placement on opposite sides of an incision.

17. The suture delivery device of claim 16, further comprising a dial configured to allow access to either the first and second needle tracks, or the third and fourth needle tracks.

18. The suture delivery device of claim 1, further comprising:
a first suture passer within the first needle track;
a second suture passer within the second needle track; and
a deployment button, wherein the deployment button is configured to advance the first and second suture passers through the first and second needle tracks, respectively.

19. A suture delivery device for suturing tissue comprising:
an elongated deployment member;
a counterforce member disposed towards a distal end of the elongated deployment member, wherein the counterforce member is configured to transition between a retracted configuration that facilitates the counterforce member entering an incision and a deployed configuration that resists extracting the counterforce member from an incision;
a compression member disposed towards a proximal end of the elongated deployment member with respect to the counterforce member, wherein the compression member is configured to resist entering an incision, and wherein the compression member is positionable along the elongated deployment member to transition between a compressed configuration and an uncompressed configuration;

a suture catcher disposed at the distal end of the elongated deployment member, wherein the suture catcher is configured to transition between a retracted configuration that facilitates the suture catcher entering an incision and a deployed configuration that facilitates catching a suture;

a first needle track extending through the compression member and oriented to direct a needle advanced through the first needle track into engagement with a first area of the suture catcher when in the deployed configuration; and a second needle track extending through the compression member and oriented to direct a needle advanced through the second needle track into engagement with a second area of the suture catcher when in the deployed configuration, wherein the first area of the suture catcher when in the deployed configuration and the second area of the suture catcher when in the deployed configuration are situated on the suture catcher to allow their placement on opposite sides of an incision.

20. A suture delivery device for suturing tissue comprising:

an elongated deployment member;

a counterforce member disposed towards a distal end of the elongated deployment member, wherein the counterforce member is configured to transition between a retracted configuration that facilitates the counterforce member entering an incision and a deployed configuration that resists extracting the counterforce member from an incision, and wherein the counterforce member includes a suture catcher;

a compression member disposed towards a proximal end of the elongated deployment member with respect to the counterforce member, wherein the compression member is configured to resist entering an incision, and wherein the compression member is positionable along the elongated deployment member to transition between a compressed configuration and an uncompressed configuration;

a first needle track extending through the compression member and oriented to direct a needle advanced through the first needle track into engagement with a first area of the suture catcher when in the deployed configuration; and a second needle track extending through the compression member and oriented to direct a needle advanced through the second needle track into engagement with a second area of the suture catcher when in the deployed configuration, wherein the first area of the suture catcher when in the deployed configuration and the second area of the suture catcher when in the deployed configuration are situated on the suture catcher to allow their placement on opposite sides of an incision.

* * * * *